(12) United States Patent
Weikert et al.

(10) Patent No.: US 6,645,958 B2
(45) Date of Patent: Nov. 11, 2003

(54) BENZOCYCLOALKYLENYLAMINE DERIVATIVES AS MUSCARINIC RECEPTOR ANTAGONISTS

(75) Inventors: Robert James Weikert, Woodside, CA (US); Ann Marie Madera, Dublin, CA (US); Russell Stephen Stabler, Mountain View, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/289,055

(22) Filed: Nov. 6, 2002

(65) Prior Publication Data

US 2003/0109524 A1 Jun. 12, 2003

Related U.S. Application Data

(62) Division of application No. 09/862,522, filed on May 22, 2001, now Pat. No. 6,500,822.
(60) Provisional application No. 60/267,617, filed on Feb. 9, 2001, and provisional application No. 60/207,483, filed on May 25, 2000.

(51) Int. Cl.[7] .................... C07D 267/02; C07D 281/02; A61K 31/55
(52) U.S. Cl. .................. 514/211.03; 540/488
(58) Field of Search ...................... 540/488; 514/211.03

(56) References Cited

U.S. PATENT DOCUMENTS

| | | | |
|---|---|---|---|
| 4,584,293 A | 4/1986 | Reiffen et al. | 514/213 |
| 4,748,182 A | 5/1988 | Hibert et al. | 514/367 |
| 4,880,802 A | 11/1989 | Schohe et al. | 514/222.2 |
| 5,047,417 A | 9/1991 | Minami et al. | 514/397 |
| 5,118,704 A | 6/1992 | Minaskanian et al. | 514/416 |
| 5,177,089 A | 1/1993 | Minami et al. | 514/357 |
| 5,298,513 A | 3/1994 | Schohe et al. | 514/319 |
| 5,382,595 A | 1/1995 | Minami et al. | 514/450 |
| 5,545,755 A | 8/1996 | Lin et al. | 564/428 |
| 5,607,953 A | 3/1997 | Minami et al. | 514/327 |

FOREIGN PATENT DOCUMENTS

WO   WO 99/43657   9/1999

OTHER PUBLICATIONS

Homan et al., "Structural Analogues of 5–Ome–BPAT: Synthesis and Interactions with Dopamine $D_2$, $D_3$, and Serotonin 5–$HT_{1A}$ Receptors", *Bioorg. Med. Chem.*, (1999), pp. 1111–1121, vol. 7(6).
Glennon et al, "N–(Phthalimidoalkyl) Derivatives of Serotonergic Agents: A Common Interaction at 5–$HT_{1A}$ Serotonin Binding Sites?", *J. Med. Chem.*, (1989), pp. 1921–1926, vol. 32.
Ehlert, et al., "Subtypes of the Muscarinic Receptor in Smooth Muscle", *Life Sciences*, (Minireview), (1997), pp. 1729–1740, vol. 61, No. 18.
Hedge, et al., "Muscarinic Receptor Subtypes Modulating Smooth Muscle Contractility in the Urinary Bladder", *Life Sciences,* (1999), pp. 419–428, 64, Nos. 6/7.
Eglen, et al., "Muscarinic acetylcholine receptor subtypes in smooth muscle", *Trends. Pharmacol. Sci.*, (1994), pp. 114–119, vol. 15.
Eglen, et al, "Muscarinic receptor subtypes and smooth muscle function", *Pharmacol. Rev.*, (1996), pp. 531–565, vol. 48, No. 4.
Nilvebrant, et al., "Tolterodine—A new Bladder Selective Muscarinic Receptor Antagonist: Preclinical Pharmacological and Clinical Data", *Life Sciences*, (1997), pp. 1129–1136, vol. 60.
Alabaster, "Discovery & Development of Selective $M_3$ Antagonists for Clinical Use", *Life Sciences,* (1997), pp. 1053–1060, vol. 60, Nos. 13/14.
Osayu, et al, "Urinary Bladder–selective Action of the New Antimuscarinic Compound Vamicamide", *Drug Res.*, (1994), pp. 1242–1249, vol. 44(II), No. 11.
Homma, et al, "Randomized Double–Blind Study to Compare Clinical Efficacy of Temiverine and Propiverine for Unstable Bladder and Detrusor Hyperreflexia", *Neurology and Urodynamics,* —Abstract, (1997), pp. 345–346, vol. 16.
Eglen and Hegde, "Selective modulation of muscarinic receptor subtypes: therapeutic potential", *Emerging Drugs,* —Chapter 4, (1998), pp. 67–79, vol. 3, Ashley Publications.
Eglen, et al, "Muscarinic receptor ligands and their therapeutic potential", *Curr. Opin. Chem. Biol.* (1999), pp. 426–432, vol. 3, Elsevier Science.
Caulfield, et al, "International Union of Pharmacology. XVII. Classification of Muscarinic Acetylcholine Receptors", *Pharmacological Reviews,* (1998), pp. 279–290, vol. 50(2).

*Primary Examiner*—Bruck Kifle
(74) *Attorney, Agent, or Firm*—Brian Buckwalter

(57) ABSTRACT

This invention relates to compounds which are generally muscarinic M2/M3 receptor antagonists and which are represented by Formula I:

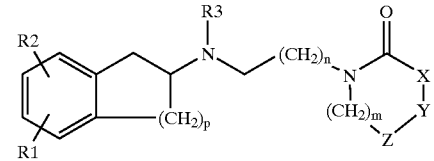

wherein X, Y, and Z are O, S, or $NR^4$, and the other substituents are as defined in the specification; and prodrugs, individual isomers, racemic or non-racemic mixtures of isomers, and pharmaceutically acceptable salts or solvates thereof. The invention further relates to pharmaceutical compositions containing such compounds and methods for their use as therapeutic agents.

13 Claims, No Drawings

BENZOCYCLOALKYLENYLAMINE DERIVATIVES AS MUSCARINIC RECEPTOR ANTAGONISTS

CROSS-REFERENCE TO RELATED INVENTIONS

This application is a divisional of Ser. No. 09/862,522 filed May 22, 2001, now U.S. Pat. No. 6,500,822, which claims benefit under Title 35 U.S.C. 119(e) of U.S. Provisional Applications Nos. 60/207,483 filed May 25, 2000; and 60/267,617 filed Feb. 9, 2001, all applications are hereby incorporated by reference in their entirety.

FIELD OF THE INVENTION

This invention relates to benzocycloalkylenylamine derivatives, associated pharmaceutically acceptable salts, or hydrates thereof, and associated pharmaceutical compositions and methods for use as M2/M3 selective muscarinic receptor antagonists.

BACKGROUND OF THE INVENTION

Acetylcholine (Ach) is the principal transmitter of the parasympathetic nervous system. The physiological actions of Ach are mediated by activation of either nicotinic or muscarinic receptors. Both of these receptor classes are heterogeneous: e.g., the muscarinic receptor family comprises five subtypes ($M_1$, $M_2$, $M_3$, $M_4$, and $M_5$) each encoded by distinct genes and possessing unique pharmacology and distribution.

Almost all smooth muscle tissues express both muscarinic M2 and M3 receptors, both of which have a functional role. M2 receptors outnumber M3 receptors by a proportion of approximately 4 to 1. Generally, M3 receptors mediate the direct contractile effects of acetylcholine in the vast majority of smooth muscle tissues. M2 receptors, on the other hand, cause smooth muscle contraction indirectly by inhibiting sympathetically (β-adrenoreceptor)-mediated relaxation.

Compounds that act as antagonists of muscarinic receptors have been used to treat several disease states associated with improper smooth muscle function. Until recently, most of these compounds have been non-selective for the various muscarinic receptor subtypes, leading to unpleasant anticholinergic side-effects such as fry mouth, constipation, blurred vision, or tachycardia. The most common of these side-effects is dry-mouth resulting from muscarinic receptor blockade in the salivary gland. Recently developed M2 or M3 specific antagonists have been shown to have reduced side effects. Evidence suggests that concurrent blockade of M2 and M3 receptors could be therapeutically effective in the treatment of disease states associated with smooth muscle disorders.

Few M2/M3 selective antagonists have been developed. The present invention fills this need by providing these types of antagonists useful in the treatment of disease states associated with improper smooth muscle function.

SUMMARY OF THE INVENTION

This invention relates to!compounds comprising Formula I:

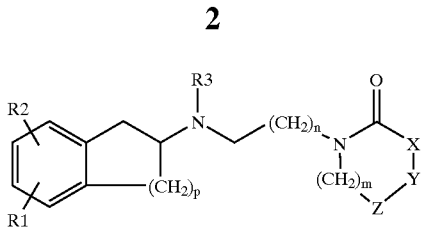

wherein:
$R^1$, and $R^2$ are independently in each occurrence hydrogen, halogen, ($C_{1-6}$)-alkyl, —OR', —SR', —NR'R", —SOR', —SO$_2$R', —COOR', —OCOR', —OCONR'R", —OCONR'R", —OSO$_2$R', —OSO$_2$NR'R"; —NR'SO$_2$R", —NR'COR", —SO$_2$NR'R", —SO$_2$(CH$_2$)$_{1-3}$CONR'R", —CONR'R", —NR'CONR'R", cyano, haloalkyl, or nitro;

R' and R" are independently in each occurrence hydrogen, ($C_{1-6}$)-alkyl, haloalkyl, aryl, heterocyclyl, heteroaryl, aryl-($C_{1-3}$)-alkyl, heteroaryl-($C_{1-3}$)-alkyl, heterocyclyl-($C_{1-3}$)-alkyl, cycloalkylalkyl, cycloalkyl, or R' and R" together with the nitrogen they are attached may also form a 5- to 7-membered ring, optionally incorporating one additional ring heteroatom chosen from N, O or $S(O)_{0-2}$;

$R^3$ is independently in each occurrence ($C_{1-6}$) alkyl, ($C_{1-6}$) alkenyl, ($C_{1-6}$) alkynyl, or cycloalkyl;

one of X, Y or Z is independently S, O, or N—$R^4$, the others are CH$_2$;

$R^4$ is hydrogen, ($C_{1-6}$)-alkyl, haloalkyl, aryl($C_{1-6}$)alkyl, heteroaryl($C_{1-6}$)alkyl, —($C_{1-6}$)—CR'R'R', —COOR', —SO$_2$R', —C(O)R', —SO$_2$(CH$_2$)$_{0-3}$NR'R", —CONR'R", or —PO(OR')$_2$, where R' and R" are as defined above;

m is an integer from 0 to 3 inclusive;
n is an integer from 1 to 6 inclusive;
p is an integer from 1 to 3 inclusive; and prodrugs, individual isomers, racemic or non-racemic mixtures of isomers, and pharmaceutically acceptable salts or solvates thereof.

In a preferred embodiment p is 2.

In another preferred embodiment p is 2, and one, of X, Y or Z is NR$^4$ and the others are CH$_2$; in another embodiment p is 2, and one of X, Y or Z is NR$^4$ and the others are CH$_2$, wherein R$^4$ is hydrogen.

In another preferred embodiment, p is 2 and m is 1; in another preferred embodiment p is 2, m is 1 and Y is NR$^4$ and the others are CH$_2$ and in another preferred embodiment p is 2, m is 1 and one of X is NH and the others are CH$_2$; in another preferred embodiment, p is 2, m is 2; in another preferred embodiment, p is 2, m is 2, and one of X, Y or Z is NR$^4$ and the others are CH$_2$, and in another preferred embodiment p is 2, m is 2, and one of X is NH and the others are CH$_2$.

In another embodiment n is 3 and p is 2, in another embodiment n is 3, and one of X, Y or Z is NR$^4$ and the others are CH$_2$; in another embodiment n is 3, p is 2 and one of X, Y, or Z is NR$^4$ and the others are CH$_2$, in another embodiment n is 3, p is 2 and one of X, Y, or Z is NH and the others are CH$_2$. In another preferred embodiment n is 3, p is 2, m is 2 and one of X, Y, or Z is NR$^4$ and the others are CH$_2$; and in another preferred embodiment n is 3, p is 2, m is 2, X is NH, and Y and Z are CH$_2$. In another preferred embodiment n is 3, p is 2, m is 2, Y is NH and X and Z are CH$_2$. In another preferred embodiment n is 3, p is 2, m is 2, Z is NH and X and Y are CH$_2$.

In another embodiment n is 3 and one of X, Y, or Z is NR$^4$ and the others are CH$_2$.

In another preferred embodiment p is 2, m is 2, n is 3, one of X, Y or Z is O and the others are CH$_2$.

In a preferred embodiment, the invention further relates to pharmaceutical compositions containing a therapeutically effective amount of at least one compound of Formula I, or prodrugs, individual isomers, racemic or non-racemic mixtures of isomers, or pharmaceutically acceptable salts or solvates thereof, in admixture with at least one suitable carrier. In a more preferred embodiment, the pharmaceutical compositions are suitable for administration to a subject having a disease state which is alleviated by treatment with a muscarinic M2/M3 receptor antagonist.

In another aspect, the invention relates to methods for treating a subject having a disease state that is alleviated by treatment with a muscarinic M2/M3 receptor antagonist, which comprises administering to such a subject a therapeutically effective amount of at least a compound of Formula I. In a preferred embodiment, the subject has a disease state comprising smooth muscle disorders; preferably genitourinary tract disorders, respiratory tract disorders, gastrointestinal tract disorders; more preferably genitourinary tract disorders such as overactive bladder or detrusor hyperactivity and its symptoms, such as the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like. In another preferred embodiment, the disease comprises respiratory tract disorders such as allergies and asthma. In another preferred embodiment, the disease state comprises gastrointestinal disorders.

In another aspect, the invention relates to a process for preparing a compound of Formula I, which process comprises reacting a compound having a general formula

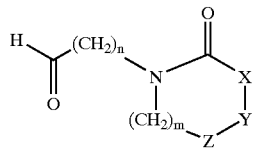

with a compound of general formula

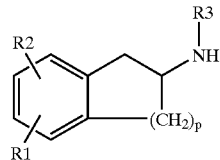

to provide a compound of Formula I:

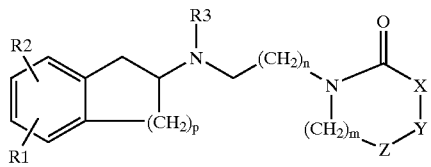

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an", and "the" include plural referents unless the context clearly dictates otherwise.

"Lower alkyl" means the monovalent linear or branched saturated hydrocarbon radical, having from one to six carbon atoms inclusive, unless otherwise indicated. Examples of lower alkyl radicals include, but are not limited to, methyl, ethyl, propyl, isopropyl, 1-ethylpropyl, sec-butyl, tert-butyl, n-butyl, n-pentyl, n-hexyl, and the like.

"Substituted lower alkyl" means the lower alkyl as defined herein, including one to three substituents, preferably one substituent such as hydroxyl, alkoxy, amino, amido, carboxyl, acyl, halogen, cyano, nitro, thiol. These groups may be attached to any carbon atom of the lower alkyl moiety. Examples of substituted lower alkyl radicals include, but are not limited to, 2-methoxyethyl, 2-hydroxyethyl, dimethylaminocarbonylmethyl, 4-hydroxy-2,2-dimethyl-butyl, trifluoromethyl, trifluorobutyl and the like.

"Alkylene" means the divalent linear or branched saturated hydrocarbon radical, having from one to six carbons inclusive, unless otherwise indicated. Examples of alkylene radicals include, but are not limited to, methylene, ethylene, propylene, 2-methyl-propylene, butylene, 2-ethylbutylene, and the like.

"Alkenyl" means the monovalent linear or branched unsaturated hydrocarbon radical, containing a double bond and having from two to six carbon atoms inclusive, unless otherwise indicated. Examples of alkenyl radicals include, but are not limited to, ethenyl, allyl, 1-propenyl, 2-butenyl, and the like.

"Alkynyl" means the monovalent linear or branched unsaturated hydrocarbon radical, containing a triple bond and having from two to six carbon atoms inclusive, unless otherwise indicated. Examples of alkynyl radicals include, but are not limited to, ethynyl, 1-propynyl, 2-butynyl, propargyl, and the like.

"Alkoxy" means the radical —O—R, wherein R is a lower alkyl radical as defined herein. Examples of alkoxy radicals include, but are not limited to, methoxy, ethoxy, isopropoxy, and the like.

"Aryl" means the monovalent aromatic carbocyclic radical consisting of one individual ring, or one or more fused rings in which at least one ring is aromatic in nature, which can optionally be substituted with one or more, preferably one or two, substituents selected from hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, biphenyl, indanyl, anthraquinolyl, tert-butyl-phenyl, 1,3-benzodioxolyl, and the like.

"Arylalkyl" means the radical R'R"—, wherein R' is an aryl radical as defined herein, and R" is an alkyl radical as defined herein. Examples of arylalkyl radicals include, but are not limited to, benzyl, phenylethyl, 3-phenylpropyl, and the like.

"Cycloalkyl" means the monovalent saturated carbocyclic radical consisting of one or more rings, preferably one or two rings, of three to eight carbons per ring, which can optionally be substituted with one or more, preferably one or two substituents, selected from hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of cycloalkyl radicals include, but are not limited to, cyclopropyl, cyclobutyl, 3-ethylcyclobutyl, cyclopentyl, cycloheptyl, and the like.

"Cycloalkylalkyl" means the radical R'R"—, wherein R' is a cycloalkyl radical as, defined herein, and R' is an alkyl radical as defined herein. Examples of cycloalkylalkyl radicals include, but are not limited to, cyclopropylmethyl, cyclohexylmethyl, cyclopentylethyl, and the like.

"Heteroaryl" means the monovalent aromatic cyclic radical having one or more rings, preferably one to three rings, of four to eight atoms per ring, incorporating one or more heteroatoms, preferably one or two, within the ring (chosen from nitrogen, oxygen, or sulfur), which can optionally be substituted with one or more, preferably one or two substituents selected from hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heteroaryl radicals include, but are not limited to, imidazolyl, oxazolyl, thiazolyl, pyrazinyl, thienyl, furanyl, pyridinyl, quinolinyl, isoquinolinyl, benzofuryl, benzothiophenyl, benzothiopyranyl, benzimidazolyl, benzoxazolyl, benzothiazolyl, benzopyranyl, indazolyl, indolyl, isoindolyl, quinolinyl, isoquinolinyl, naphthyridinyl, benezenesulfonyl-thiophenyl, and the like.

"Heteroarylalkyl" (or "heteroaralkyl") means the radical of the formula R'R", wherein R' is a heteroaryl radical as defined herein, and R" is an alkylene radical as defined herein. Examples of heteroarylalky radicals include, but are not limited to, 2-imidazolylmethyl, 3-pyrrolylethyl, and the like.

"Heterocyclyl" means the monovalent saturated cyclic radical, consisting of one or more rings, preferably one to two rings, of three to eight atoms per ring, incorporating one or more ring heteroatoms (chosen from N,O or $S(O)_{0-2}$), and which can optionally be substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, morpholinyl, piperazinyl, piperidinyl, pyrrolidinyl, tetrahydropyranyl, thiomorpholinyl, quinuclidinyl, and the like.

"Heterocycloalkyl" (or "heterocyclylalkyl") means the radical of the formula R'R", wherein R' is a heterocyclic radical as defined herein, and R" is an alkylene radical as defined herein. Examples of heterocycloalkyl radicals include, but are not limited to, 1-piperazinylmethyl, 2-morpholinomethyl, and the like.

"Halogen" means the radical fluoro, bromo, chloro, and/or iodo.

"Haloalkyl" means the lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Hydroxyalkyl" means the lower alkyl radical as defined herein, substituted with one or more hydroxy groups. Examples of hydroxyalkyl radicals include, but are not limited to, hydroxymethyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, and 2-(hydroxymethyl)-3-hydroxypropyl, and the like.

"Acyloxy" means the radical —OC(O)R, wherein R is a lower alkyl radical as defined herein. Examples of acyloxy radicals include, but are not limited to, acetoxy, propionyloxy, and the like.

"Alkoxycarbonyl" or "alkyl ester" means the radical —C(O)—O—R, wherein R is a lower alkyl radical as defined herein. Examples of alkoxycarbonyl radicals include, but are not limited to, methoxycarbonyl, ethoxycarbonyl, sec-butoxycarbonyl, isopropyloxycarbonyl, and the like.

"Aryloxycarbonyl" or "aryl estern means the radical —C(O)—O—R, wherein R is an aryl radical as defined herein. Examples of aryloxycarbonyl radicals include, but are not limited to phenyl ester, naphthyl ester, and the like.

"Arylalkoxycarbonyl" or "arylalkyl ester" means the radical —C(O)—O—RR', wherein R is a lower alkyl radical and R' is an aryl radical as defined herein. Examples of aryloxycarbonyl radicals include, but are not limited to benzyl ester, phenyl ethyl ester, and the like.

"Alkylcarbonyl" (or "acyl") means the radical R—C(O)—, wherein R is a lower alkyl radical as defined herein. Examples of alkylcarbonyl radicals include, but are not limited to, acetyl, propionyl, n-butyryl, sec-butyryl, t-butyryl, iso-propionyl and the like., "Arylcarbonyl" means the radical R—C(O)—, wherein R is an aryl radical as defined herein. Examples of arylcarbonyl radicals include, but are not limited to, benzoyl, naphthoyl, and the like.

"Arylalkylcarbonyl" (or "aralkylcarbonyl") means the radical R—C(O)—, wherein R is an arylalkyl radical as defined herein. Examples of arylalkylcarbonyl radicals include, but are not limited to, phenylacetyl, and the like.

"Heteroarylcarbonyl" means the radical R—C(O)—, wherein R is an heteroaryl radical as defined herein. Examples of heteroarylcarbonyl radicals include, but are not limited to, pyridinoyl, 3-methylisoxazoloyl, isoxazoloyl, thienoyl, furoyl, and the like.

"Heterocyclylcarbonyl" (or "heterocyclocarbonyl") means the radical R—C(O)—, wherein R is an heterocyclyl radical as defined herein. Examples of heterocyclylcarbonyl radicals include, but are not limited to, piperazinoyl, morpholinoyl, pyrrolindinoyl, and the like.

"Cycloalkylcarbonyl" means the radical R—C(O)—, wherein R is a cycloalkyl radical as defined herein. Examples of cycloalkylcarbonyl radicals include, but are not limited to, cyclobutanoyl, cyclopentanoyl, cyclohexanoyl, and the like.

"Alkylaminocarbonyl" means the radical —C(O)NR'R', wherein R' is lower alkyl as defined herein, and Ru is hydrogen or lower alkyl as defined herein. Examples of akylaminocarbonyl include, but are not limited to methylaminocarbonyl, dimethylaminocarbonyl, t-butylaminocarbonyl, n-butylaminocarbonyl, iso-propylaminocarbonyl and the like.

"Arylaminocarbonyl" means the radical —C(O)NR'R", wherein R' is aryl as defined herein, and R" is hydrogen or aryl as defined herein. Examples of arylaminocarbonyl include, but are not limited to phenylaminocarbonyl, methoxyphenylaminocarbonyl, diphenylaminocarbonyl, dimethoxyphenylaminocarbonyl, and the like.

"Heteroarylaminocarbonyl" means the radical —C(O)NR'R', wherein R' is heteroaryl as defined herein, and R" is hydrogen or heteroaryl as defined herein. Examples of heteroarylaminocarbonyl include, but are not limited to pyridinylaminocarbonyl, thienylaminocarbonyl, furanylaminocarbonyl, and the like.

"Alkylcarbonylamino" means the radical —NC(O)R', wherein R' is lower alkyl as defined herein. Examples of alkylcarbonylamino include, but are not limited to methylcarbonylamino, iso-propylcarbonylamino, t-butylcarbonylamino, and the like.

"Arylcarbonylamino" means the radical —NC(O)R', wherein R' is aryl as defined herein. Examples of arylcarbonylamino include, but are not limited to phenylcarbonylamino, tosylcarbonylamino, and the like.

"Alkylcarbamoyl" means the radical —OC(O)NR'R", wherein R' is lower alkyl as defined herein, and R" is hydrogen or lower alkyl as defined herein. Examples of alkylcarbamoyl include, but are not limited to methylcarbamoyl, ethylcarbamoyl, and the like.

"Arylcarbamoyl" means the radical —OC(O)NR'R", wherein R' is lower aryl as defined herein, and R" is hydrogen or aryl as defined herein. Examples of arylcarbamoyl include, but are not limited to phenylcarbamoyl, naphthylcarbamoyl, and the like.

"Arylalkylcarbamoyl" means the radical —OC(O)NHR'R", wherein R' is lower alkyl as defined herein, and R" is aryl as defined herein. Examples of arylalkylcarbamoyl include, but are not limited to benzylcarbamoyl, phenylethylcarbamoyl, and the like.

"Alkylaminosulfonyl" means the radical —S(O)$_2$NR'R", wherein R' is lower alkyl as defined herein, and R" is hydrogen or lower alkyl as defined herein. Examples of alkylaminosulfonyl include, but are not limited to methylaminosulfonyl, dimethylaminosulfonyl, and the like.

"Arylaminosulfonyl" means the radical —S(O)$_2$NR'R", wherein R' is aryl as defined herein, and R" is hydrogen or aryl as defined herein. Examples of arylaminosulfonyl include, but are not limited to phenylaminosulfonyl, methoxyphenylaminosulfonyl, and the like.

"Heteroarylaminosulfonyl" means the radical —S(O)$_2$NR'R", wherein R' is heteroaryl as defined herein, and R' is hydrogen or heteroaryl as defined herein. Examples of heteroarylaminosulfonyl include, but are not limited to thienylaminosulfonyl, piperidinylaminosulfonyl, furanylaminosulfonyl, imidazolylaminosulfonyl and the like.

"Alkylsulfonylamino" means the radical —NS(O)$_2$R', wherein R' is lower alkyl as defined herein. Examples of alkylsulfonylamino include, but are not limited to methylsulfonylamino, propylsulfonylamino, and the like.

"Arylsulfonylamino" means the radical —NS(O)$_2$R', wherein R' is aryl as defined herein. Examples of arylsulfonylamino include, but are not limited to phenylsulfonylamino, naphthylsulfonylamino, and the like.

"Alkylsulfonyl" means the radical —S(O)$_2$R, wherein R is lower alkyl or a substituted lower alkyl as defined herein. Examples of alkylsulfonyl include, but are not limited to methylsulfonyl, trifluoromethylsulfonyl, propylsulfonyl, and the like.

"Arylsulfonyl" means the radical —S(O)$_2$R, wherein R is aryl as defined herein. Examples of arylsulfonyl include, but are not limited to phenylsulfonyl, nitrophenylsulfonyl, methoxyphenylsulfonyl, 3,4,5-trimethoxyphenylsulfonyl, and the like.

"Heteroarylsulfonyl" means the radical —S(O)$_2$R, wherein R is heteroaryl as defined herein. Examples of heteroarylsulfonyl include, but are not limited to thienylsulfonyl, furanylsulfonyl, imidazolylsulfonyl, N-methylimidazolylsulfonyl and the like.

"Heterocyclylsulfonyl" means the radical —S(O)$_2$R, wherein R is heterocyclyl as defined herein. Examples of heterocyclylsulfonyl include, but are not limited to piperidinylsulfonyl, piperazinylsulfonyl, and the like.

"Alkylsulfonyloxy" means the radical —O S(O)$_2$R, wherein R is lower alkyl or substituted lower alkyl as defined herein. Examples of alkylsulfonyloxy include, but are not limited to methylsulfonyloxy, trifluoromethylsulfonyloxy, propylsulfonyloxy, and the like.

"Arylsulfonyloxy" means the radical —O S(O)$_2$R, wherein R is aryl as defined herein. Examples of arylsulfonyloxy include, but are not limited to benzenesulfonyloxy., 4-chloro-benzenesullfonyloxy, and the like "Heteroarylsulfonyloxy" means the radical —O S(O)$_2$R, wherein R is hetroaryl as defined herein. Examples of hetroarylsulfonyloxy include, but are not limited to thienylsulfonyloxy, and the like. "Heterocyclylsulfonyloxy" means the radical —O S(O)$_2$R, wherein R is heterocycyl as defined herein. Examples of heterocyclylsulfonyloxy include, but are not limited to 3,5,dimethyl-isoxazolesulfonyloxy, pyrrolidinylsulfonyloxy, and the like.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Leaving group" means the group with the meaning conventionally associated with it in synthetic organic chemistry, i.e., an atom or group displaceable under alkylating conditions. Examples of leaving groups include, but are not limited to, halogen, alkyl- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive oxygen atoms present in the reactants. Acceptable protective groups for alcoholic or phenolic hydroxyl groups, which may be removed successively and selectively includes groups protected as acetates, haloalkyl carbonates, benzyl ethers, alkylsilyl ethers, heterocyclyl ethers, and methyl or alkyl ethers, and the like. Protective or blocking groups for carboxyl groups are similar to those described for hydroxyl groups, preferably tert-butyl, benzyl or methyl esters. Examples of protecting groups can be found in T. W. Greene et al., *Protective Groups in Organic Chemistry*, (J. Wiley, $2_{nd}$ ed. 1991) and Harrison et al., *Compendium of Synthetic Organic Methods*, Vols. 1–8 (J. Wiley and Sons 1971–1996).

"Amino-protecting group" means the protecting group that refers to those organic groups intended to protect the nitrogen atom against undesirable reactions during synthetic procedures and includes, but is not limited to, benzyl, benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like. It is preferred to use either BOC or CBZ as the amino-protecting group because of the relative ease of removal, for example by mild acids in the case of BOC, e.g., trifluoroacetic acid or hydrochloric acid in ethyl acetate; or by catalytic hydrogenation in the case of CBZ.

"Deprotection" or "deprotecting" means the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxide in alcoholic solutions, zinc in methanol, acetic acid, trifluoroacetic acid, palladium catalysts, or boron tribromide, and the like.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al. (1966) *Angew. Chem. Inter.* Edit., 5, 385; errata 511; Cahn et al. (1966) *Angew. Chem.*, 78, 413; Cahn and Ingold (1951) *J. Chem. Soc.* (London), 612; Cahn et al. (1956) *Experientia.* 12, 81; Cahn, J. (1964) *Chem. Educ.*, 41,116).

"Geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

"Atropic isomers" means the isomers owing their existence to restricted rotation caused by hindrance of rotation of large groups about a central bond.

"Substantially pure" means at least about 80 mole percent, more preferably at least about 90 mole percent, and most preferably at least about 95 mole percent of the desired enantiomer or stereoisomer is present.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

(1) acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluenesulfonic acid, trimethylacetic acid, trifluoroacetic acid, and the like; or (2) salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from hydrochloric acid, trifluoroacetic acid, dibenzoyl-L-tartaric acid, and phosphoric acid.

It should be understood that all references to pharmaceutically acceptable salts include solvent addition forms (solvates) or crystal forms (polymorphs) as defined herein, of the same acid addition salt.

"Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density hardness, crystal shape, optical and electrical properties, stability and solubility. Recrystallization solvent, rate of crystallization, storage temperature, and other factors may cause one crystal form to dominate.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. "Prodrug" means a pharmacologically inactive form of a compound which must be metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described in *The Organic Chemistry of Drug Design and Drug Action*, by Richard B. Silverman, Academic Press, San Diego, 1992. Chapter 8: "Prodrugs and Drug delivery Systems" pp.352–401; *Design of Prodrugs*, edited by H. Bundgaard, Elsevier Science, Amsterdam, 1985; *Design of Biopharmaceutical Properties through Prodruqs and Analogs*. Ed. by E. B. Roche, American Pharmaceutical Association, Washington, 1977; and *Drug Delivery Systems*, ed. by R. L. Juliano, Oxford Univ. Press, Oxford, 1980.

"Subject" means mammals and non-mammals. Mammals means any member of the Mammalia class including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like.

"Therapeutically effective amount" means an amount of a compound that, when administered to a subject for treating a disease state, is sufficient to effect such treatment for the disease state. The "therapeutically effective amount" will vary depending on the compound, and disease state being treated, the severity or the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. In one preferred embodiment, a pharmacological effect means that primary indications of the subject being treated are prevented, alleviated, or reduced. For example, a pharmacological effect would be one that results in the prevention, alleviation or reduction of primary indications in a treated subject. In another preferred embodiment, a pharmacological effect means that disorders or symptoms of the primary indications of the subject being treated are. prevented, alleviated, or reduced. For example, a pharmacological effect would be one that results in the prevention or reduction of primary indications in a treated subject.

"Disease state" means any disease, condition, symptom, or indication.

"Treating" or "treatment" of a disease state includes:
(1) preventing the disease state, i.e. causing the clinical symptoms of the disease state not to develop in a subject that may be exposed to or predisposed to the disease state, but does not yet experience or display symptoms of the disease state;
(2) inhibiting the disease state, i.e., arresting the development of the disease state or its clinical symptoms; or
(3) relieving the disease state, i.e., causing temporary or permanent regression of the disease state or its clinical symptoms.

"Antagonist" means a molecule such as a compound, a drug, an enzyme inhibitor, or a hormone, that diminishes or prevents the action of another molecule or receptor site.

"Disorders of the urinary tract" or "uropathy" used interchangeably with "symptoms of the urinary tract" means the pathologic changes in the urinary tract. Symptoms of the urinary tract include overactive bladder (also known as detrusor hyperactivity), outlet obstruction, outlet insufficiency, and pelvic hypersensitivity.

"Overactive bladder" or "Detrusor hyperactivity" includes, but is not limited to, the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

"Outlet obstruction" includes, but is not limited to, benign prostatic hypertrophy (BPH), urethral stricture disease, tumors and the like. It is usually symptomatically manifested as obstructive (low flow rates, difficulty in initiating urination, and the like), or irritative (urgency, suprapubic pain, and the like).

"Outlet insufficiency" includes, but is not limited to, urethral hypermobility, intrinsic sphincteric deficiency, or mixed incontinence. It is usually symptomatically manifested as stress incontinence.

"Pelvic Hypersensitivity" includes but is not limited to, pelvic pain, interstitial (cell) cystitis, prostadynia, prostatis, vulvadyina, urethritis, orchidalgia, and the like. It is symptomatically manifested as pain, inflammation or discomfort referred to the pelvic region, and usually includes symptoms of overactive bladder.

Nomenclature

The naming of the compounds of this invention is illustrated below:

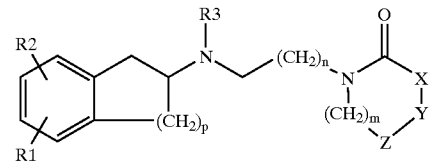

In general, the nomenclature used in this Application is based on AUTONOM™, a Beilstein Institute computerized system for the generation of IUPAC systematic nomenclature.

A compound of Formula I wherein $R^1$ and $R^2$ are methoxy, $R^3$ is propyl, p is 2, n is 3, m is 2, X and Y are $CH_2$ and Z is NH is named: 4-{4-[(6,7-dimethoxy-1,2,3,4-tetrahydro-naphthalen-2-yl)-propyl-amino]-butyl}-[1,4]diazepan-5-one.

Preferred Compounds

Among compounds of the present invention set forth in the Summary of the Invention, certain compounds of Formula I, or prodrugs, individual isomers, racemic or non-racemic mixtures of isomers, or pharmaceutically acceptable salts or solvates thereof, are preferred:

$R^1$, and $R^2$ are independently in each occurrence preferably hydrogen, halogen, $(C_{1-6})$-alkyl, alkoxy, alkylsulfonyl, or alkylsulfonyloxy, and more preferably hydrogen, methoxy, methylsulfonyl, or methylsulfonyloxy.

$R^3$ is independently in each occurrence preferably lower alkyl, lower alkenyl or lower alkynyl, more preferably ethyl, propyl, iso-propyl, allyl or propargyl, and even more preferably ethyl or propyl.

p is preferably 1 to 3, more preferably 1 to 2, and even more preferably 2.

m is preferably 0 to 3; more preferably 1 to 2; and even more preferably 2.

n is preferably 1 to 6; more preferably 1 to 3; and even more preferably 3.

one of X, Y, or Z is independently in each occurrence preferably S, O, or $NR^4$, most preferably $NR^4$, and even more preferably NH.

Other preferred compounds of the present invention include the pharmaceutically acceptable salts of the compounds of the present invention wherein the pharmaceutically acceptable salts are formed from hydrochloric acid, 2,2,2-trifluoroacetic acid, dibenzoyl-L-tartaric acid, sodium, or phosphoric acid, more preferably the salts are formed from hydrochloric acid, 2,2,2-trifluoroacetic acid.

Exemplary particularly preferred compounds, or prodrugs, individual isomers, racemic or non-racemic mixtures of isomers, or pharmaceutically acceptable salts or solvates thereof, include:

3,5-dimethyl-isoxazole-4-sulfonic acid 7-{[4-(7-oxo-[1,4]diazepan-1-yl)-butyl]-propyl-amino}-5,6,7,8-tetrahydro-naphthalen-2-yl ester;

4-(2-dimethylamino-ethanesulfonyl)-1-{4-[(7-methoxy-1,2,3,4-tetrahydro-naphthalen-2-yl)-propyl-amino]-butyl}-[1,4]diazepan-2-one;

4-{4-[(7-methoxy-1,2,3,4-tetrahydro-naphthalen-2-yl)-propyl-amino]-butyl}-[1,4]diazepan-5-one;

4-{5-[(7-methoxy-1,2,3,4-tetrahydro-naphthalen-2-yl)-propyl-amino]-pentyl}-[1,4]diazepan-5-one;

1-{4-[(7-methoxy-1,2,3,4-tetrahydro-naphthalen-2-yl)-propyl-amino]-butyl}-[1,4]diazepan-2-one;

1-{4-[(7-bromo-1,2,3,4-tetrahydro-naphthalen-2-yl)-propyl-amino]-butyl}-[1,4]diazepan-2-one; or 3-{4-[(6,7-dimethoxy-1,2,3,4-tetrahydro-naphthalen-2-yl)-propyl-amino]-butyl}-[1,3]oxazepan-2-one.

GENERAL SYNTHETIC REACTION SCHEMES

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as Fieser and Fieser (1991) *Reagents for Organic Synthesis*; Wiley & Sons: New York, Volumes 1–15; Rodd (1989) *Chemistry of Carbon Compounds*. Elsevier Science Publishers, Volumes 1–5 and Supplementals; and (1991) *Organic Reactions*, Wiley & Sons: New York, , Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to about 125° C., and most preferably and conveniently at about room (or ambient) temperature, e.g., about 20° C.

Scheme A

Scheme A, in general, describes a method of preparing a compound of Formula I wherein X, Y, Z, $R^1$, $R^2$, $R^3$, p, m, and n are as described in the Summary of the Invention.

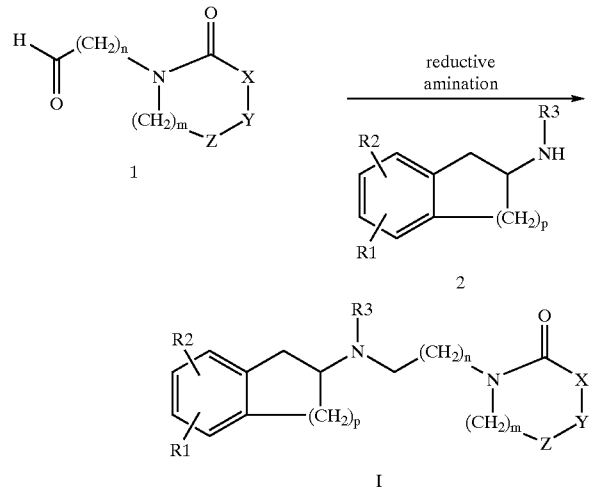

A compound of Formula I can generally be prepared by coupling a carboxaldehyde 1 with a benzocyclylamine 2 under reductive amination conditions. Suitable reducing conditions include sodium triacetoxyborohydride, sodium cyanoborohydride, titanium isopropoxide and sodium cyanoborohydride, hydrogen and a metal catalyst and hydrogen transfering agents such as cyclohexene, formic acid and its salts, zinc and hydrochloric acid, formic acid, or borane dimethylsulfide followed by treatment with formic acid. Suitable inert organic solvents for the reaction include dichloromethane, 1,2-dichloroethane, tetrahydrofuran, alcohols, or ethyl acetate, and the like. Preferably the reaction is carried out under basic conditions with sodium triacetoxyborohydride in 1,2-dichloroethane.

Reductive amination procedures are described in the chemical literature. For example, (1996) *J. Org. Chem.*, 61, 3849 and (1996) *Tetrahedron Letters*, 37, 3977, describe methods utilizing sodium triacetoxyborohydride as a reagent for the reductive amination of aldehydes with a wide variety of amines. For example, (1971) *J. Am. Chem. Soc.*, 93, 2897 and (1988) *Org. Synth. Coll.*, 6, 499 describe methods utilizing sodium cyanoborohydride as reagent for reductive amination of carbonyl compounds.

The conventional starting materials of Scheme A are commercially available or are known to, or can readily be synthesized by those of ordinary skill in the art. For example, the starting carboxaldehyde 1 can readily be synthesized as shown by the following reaction schemes (1), (2), and (3):

(1)

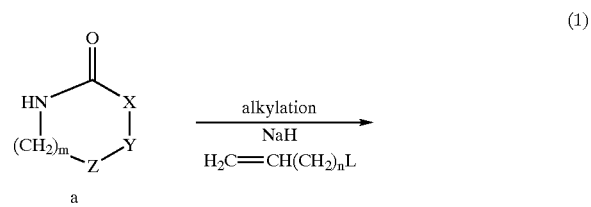

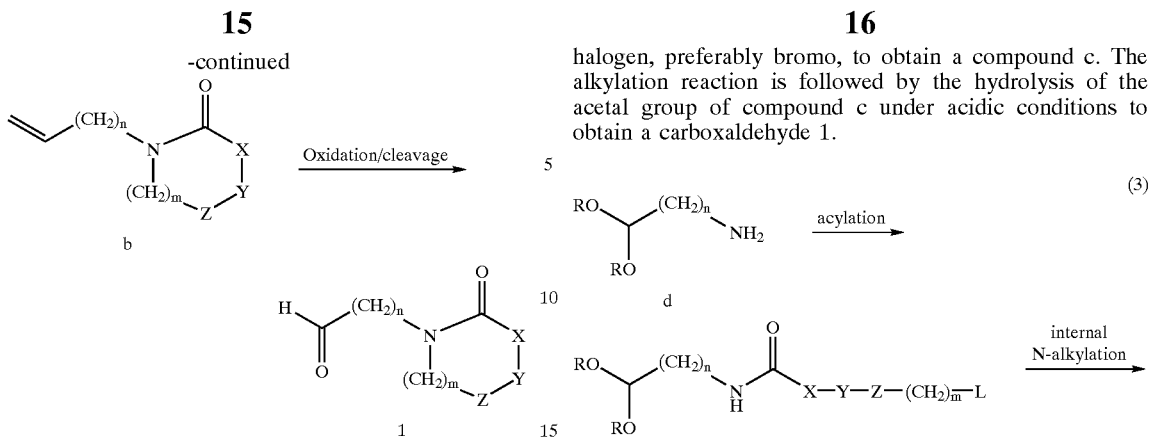

A carboxaldehyde 1 wherein X, Y, Z, m, and n are as described in the Summary of the Invention can be prepared by reacting the amido group of compound a with an alkylating agent of the formula $L(CH_2)_nCH=CH_2$ wherein L is a leaving group such as halogen or methanesulfonyloxy, preferably chloro, under basic conditions to obtain a compound b. The alkylation reaction is followed by the oxidation/cleavage of the terminal alkene group of compound b to an aldehyde group to obtain a carboxaldehyde 1. Various oxidizing agents used in the oxidation/cleavage of alkenes to aldehydes are described in the chemical literature. For example, (1956) *J. Org. Chem.*, 21, 478 describes methods utilizing osmium tetroxide and sodium (meta) periodate; (1982) *Syn. Comm.*, 12,1063 describes methods utilizing potassium permanganate and sodium(meta) periodate; (1987) *J. Org. Chem.*, 52, 3698 describes methods utilizing potassium permanganate and silica gel; (1958) *Chem. Rev.*, 58, 925 describes methods utilizing ozone; (1986) *J. Org. Chem.*, 51, 3213 describes methods utilizing potassium permanganate alone; (1987) *J. Org. Chem.*, 52, 2875 describes methods utilizing sodium (meta)periodate and catalytic ruthenium. Preferably the reaction is carried out with osmium tetroxide and sodium (meta)periodate or ozone.

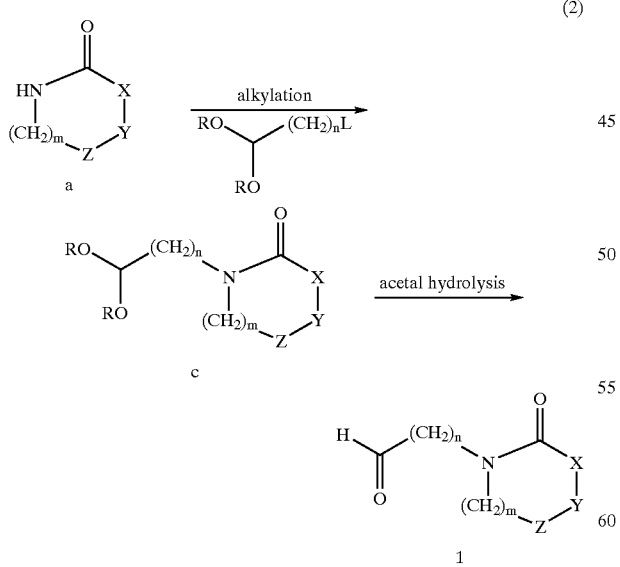

Alternatively, a carboxaldehyde 1 wherein X, Y, Z, m, and n are as described in the Summary of the Invention can be prepared by reacting the free amine group of compound a with an alkylating agent of the formula $L(CH_2)_nC(OR)_2$ wherein R is lower alkyl and L is a leaving group such as halogen, preferably bromo, to obtain a compound c. The alkylation reaction is followed by the hydrolysis of the acetal group of compound c under acidic conditions to obtain a carboxaldehyde 1.

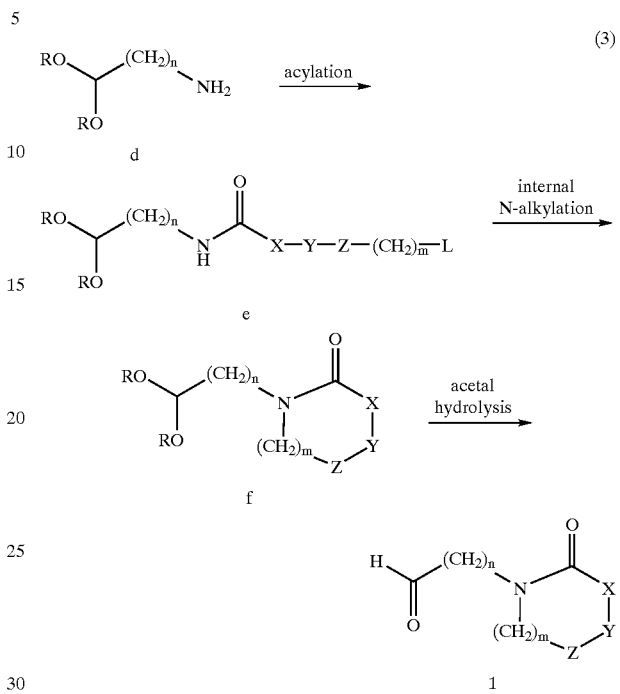

Alternatively, a carboxaldehyde 1 wherein X, Y, Z, m, and n are as described in the Summary of the Invention, can be prepared by treating an aminoacetal d wherein R is lower alkyl with an appropriate acylating agent such as acylating agents of the formula $L(CH_2)_nCOL'$, or $L(CH_2)_nOCOL'$, or $L(CH_2)_nN=C=O$ wherein in each instance L' is a leaving group such as halogen, preferably chloro, to obtain compound e. The acylating reaction is followed by the internal N-alkylation of compound e, and the subsequent hydrolysis of the acetal group of compound f to obtain a carboxaldehyde 1.

For example, the starting benzocyclylamine 2 can be synthesized as shown by the following reaction scheme (4):

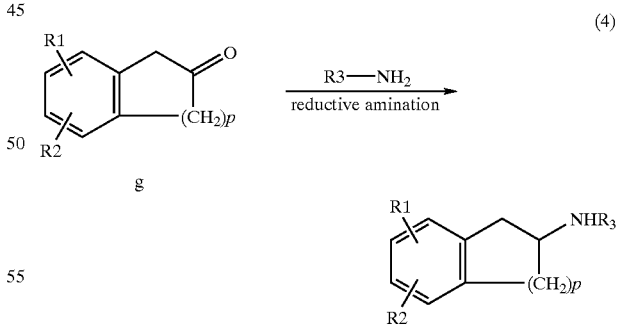

A benzocyclylamine 2 wherein $R^1$, $R^2$, and $R^3$, are as described in the Summary of the Invention may be prepared by treatment of a benzocyclylone g with a primary amine of the formula $R^3NH_2$ under reductive amination conditions. Various methods for the synthesis of a benzocyclylamine 2 are described in the chemical literature, for example, (1980) *J. Med. Chem.*, 23, 745–749; (1981) *J. Med. Chem.*, 24, 429–434; (1989) *J. Med. Chem.*, 32, 2128–2134, (1996) J.

Org. chem., 61, 3849–3862. and (1997) *Bioorg. Med Chem.Lett.*, 15, 1995–1998.

Scheme B

Scheme B, in particular, describes a method of preparing a compound of Formula I wherein X is $NR^4$, O, or S; Y and Z are each $CH_2$; and $R^1$, $R^2$, $R^3$, $R^4$, p, m, and n are as described in the Summary of the Invention.

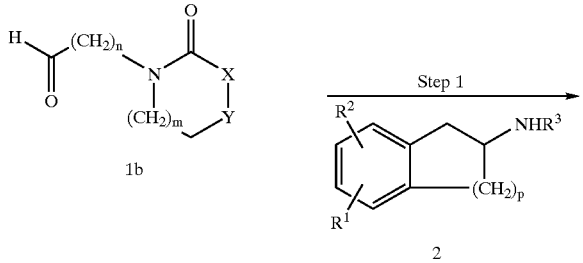

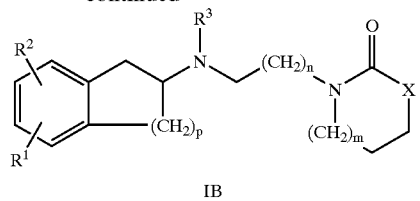

A compound of Formula IB can be prepared by proceeding as described in Scheme A. Preferably, a compound of Formula IB can be prepared by reacting a carboxaldehyde 1b with a benzocyclylamine 2 under reductive amination conditions as described in Scheme A.

Exemplary preparations of a compound of Formula IB are given in Example 1.

Scheme C

Scheme C, in particular, describes a method of preparing a compound of Formula I wherein X and Z are $CH_2$, Y is $NR^4$, O or S, and $R^1$, $R^2$, $R^3$, $R^4$, p, m, and n are as described in the Summary of the Invention.

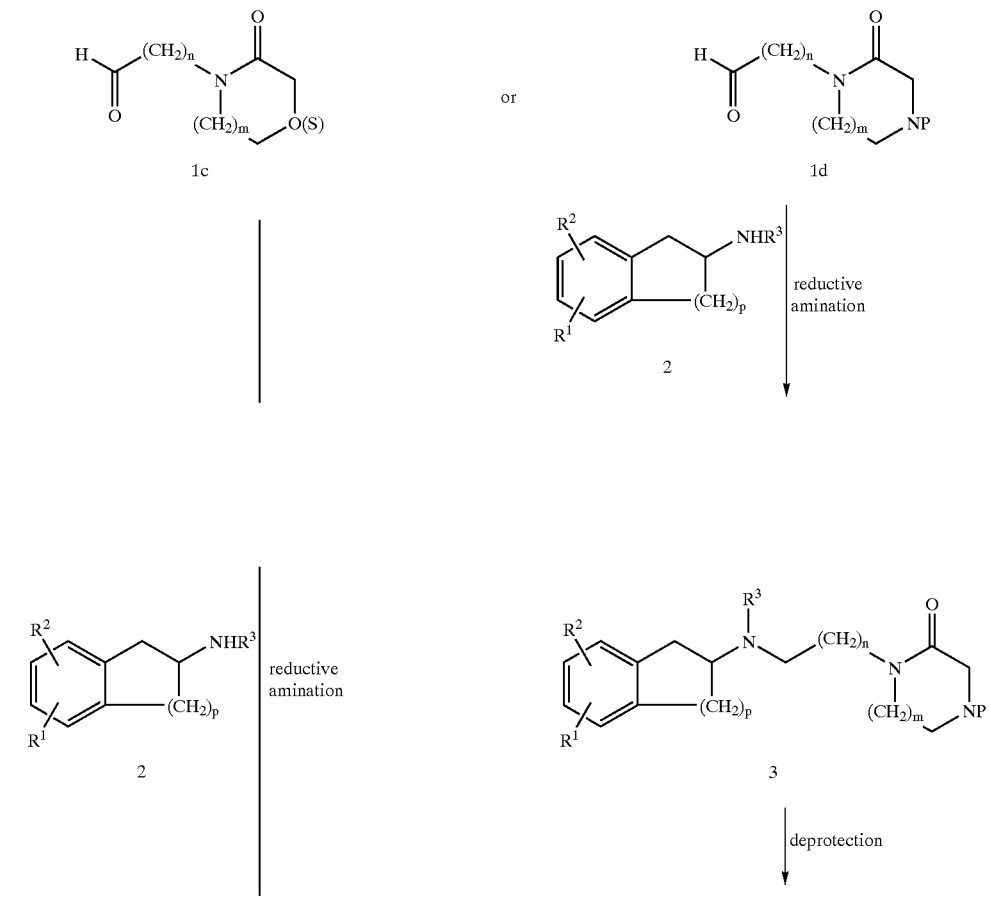

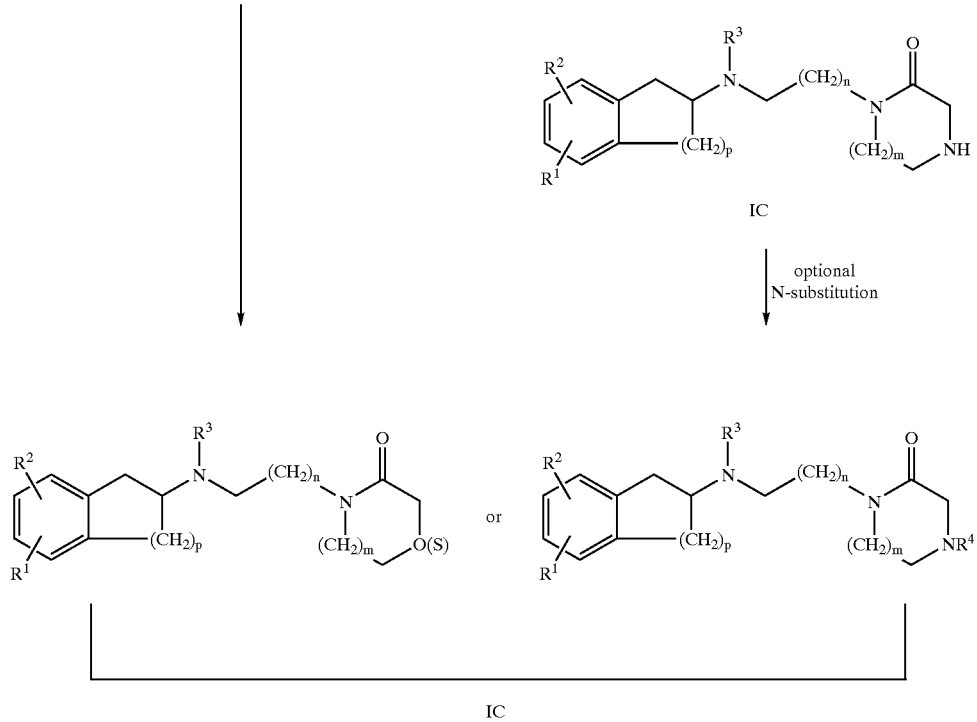

IC

IC

A compound of Formula IC can be prepared by proceeding as described in Scheme A.

Preferably, a compound of Formula I wherein Y is O or S can be prepared by reacting a carboxaldehyde 1 c with a benzocyclylamine 2 under reductive amination conditions as described in Scheme A.

Alternatively, a compound of Formula I wherein Y is $NR^4$ can also be prepared by coupling a nitrogen-protected carboxaldehyde 1d wherein P is a suitable nitrogen-protecting group with a benzocylcylamine 2 in conditions as described above. This reaction is followed by removing the nitrogen-protecting group of compound 3under acidic conditions to obtain a compound of Formula I wherein Y is NH. The compound of Formula I wherein Y is NH may then be further reacted with an appropriate alkylating agent, acylating agent, or sulfonylating agent by procedures known to one skilled in the art to obtain a compound of Formula I wherein Y is $NR^4$ wherein $R^4$ is other than H.

Exemplary preparations of a compound of Formula IC are given in Examples 2, 3, and 4.

Scheme D
Scheme D, in particular, describes a method of preparing a compound of Formula I wherein X and Y are $CH_2$, and Z is $NR^4$, O or S, and $R^1$, $R^2$, $R^3$, $R^4$, p, m, and n are as described in the Summary of the Invention.

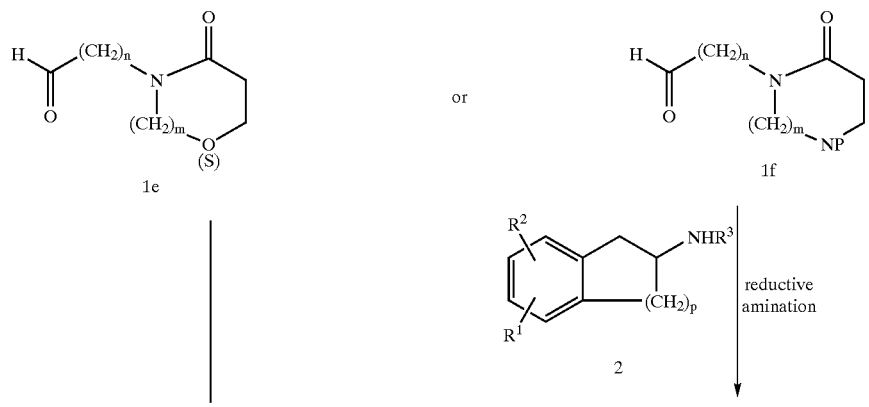

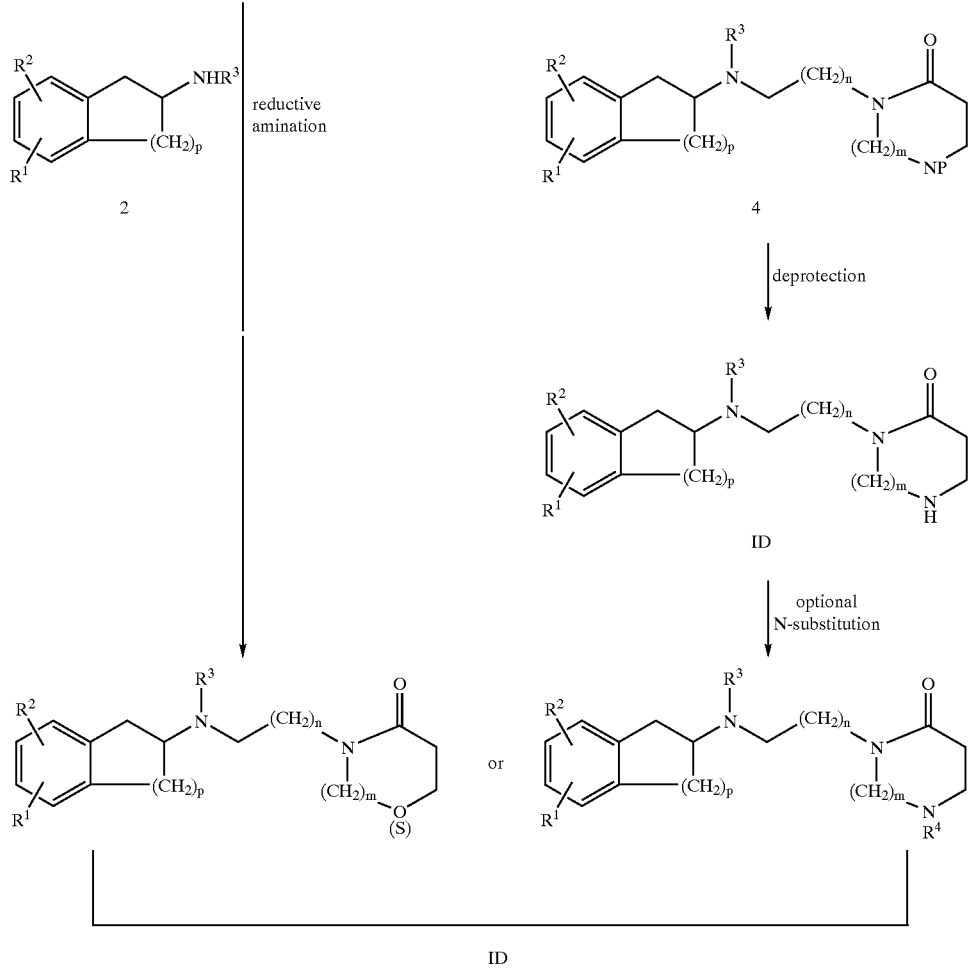

A compound of Formula ID can be prepared by proceeding as described in Scheme A.

Preferably, a compound of Formula I wherein Z is O or S can be prepared by reacting a carboxaldehyde 1e with a benzocyclylamine 2 under conditions as described in Scheme A.

Alternatively, a compound of Formula I wherein Z is $NR^4$ can be prepared by coupling an amino-protected carboxaldehyde 1f wherein P is a suitable nitrogen-protecting group with a benzocyclylamine 2 as mentioned above. This reaction is followed by removing the nitrogen-protecting group of compound 4 under acidic conditions to obtain a compound of Formula I wherein Z is NH. Optionally the compound of Formula I wherein Z is NH may then be further reacted with an appropriate alkylating agent, acylating agent, or sulfonylating agent by procedures known to one skilled in the art to obtain a compound of Formula I wherein Z is $NR^4$ wherein $R^4$ is other than H.

Exemplary preparations of a compound of Formula ID are given in.Examples 5, 6, and 7.

GENERAL UTILITY

Compounds that act as antagonists of muscarinic receptors have been used to treat several disease states associated with improper smooth muscle function. Until recently, most of these compounds have been non-selective for the various muscarinic receptor subtypes, leafing to unpleasant anticholinergic side-effects such as dry mouth, constipation, blurred vision or tachycardia, the most common of which is dry-mouth that results from muscarinic receptor blockade in the salivary gland. Recently developed M2 or M3 specific antagonists have been shown to have reduced side effects. Evidence suggests that concurrent blockade of M2 and M3 receptors could be therapeutically effective in the treatment of disease states associated with smooth muscle disorders, such as genitourinary tract disorders respiratory tract disorders, gastrointestinal tract disorders, and smooth muscle disorders.

Genitourinary tract disorders treatable with compounds of this invention specifically include overactive bladder or detrusor hyperactivity and its symptoms such as the changes symptomatically manifested as urgency, frequency, reduced bladder capacity, incontinence episodes, and the like; the changes urodynamically manifested as changes in bladder capacity, micturition threshold, unstable bladder contractions, sphincteric spasticity, and the like; and the symptoms usually manifested in detrusor hyperreflexia (neurogenic bladder), in conditions such as outlet obstruction, outlet insufficency, pelvic hypersensitivity, or in idiopathic conditions such as detrusor instability, and the like.

Gastrointestinal tract disorders treatable with compounds of this invention specifically include irritable bowel syndrome, diverticular disease, achalasia, gastrointestinal hypermotility disorders, and diarrhea. Respiratory tract disorders treatable with compounds of this invention specifically include chronic obstructive pulmonary disease, asthma and pulmonary fibrosis.

These and other therapeutic uses are described, for example, in Goodman & Gilman, (1996) *The Pharmacological Basis of Therapeutics*, ninth edition, McGraw-Hill, New York, Chapter 26:601–616; and Coleman, R. A., (1994) *Pharmacological Reviews*, 46:205–229.

TESTING

The compounds of this invention are muscarinic receptor antagonists. The muscarinic receptor affinity of test compounds can be determined by an in vitro receptor binding assay which utilizes a cell membrane preparation from the Chinese hamster ovary cells expressing the recombinant human muscarinic receptors ($M_1$–$M_5$), and is described in more detail in Example 15.

The muscarinic antagonist properties of the test compounds can be identified by an in vivo assay which determines inhibitory activity against muscarinic receptor mediated saliva secretion in anesthetized rats, and is described in more detail in the Oxotremorine/Pilocarpine-induced salivation (OIS/PIS) model in anesthetized rats, Example 16.

The muscarinic antagonist properties of the test compounds can be identified by an in vivo assay which determines inhibitory activity against muscarinic receptor mediated bladder contraction in anesthetized rats, and is described in more detail in the inhibition of volume-induced contractions assay, Example 17.

The muscarinic antagonist properties of the test compounds can be identified by an in vivo assay which determines inhibitory activity against muscarinic receptor mediated bladder contraction and saliva secretion in anesthetized dogs, and is described in more detail in Example 18.

ADMINISTRATION AND PHARMACEUTICAL COMPOSITION

The present invention includes pharmaceutical compositions comprising at least one compound of the present invention, or a prodrug, an individual isomer, a racemic or non-racemic mixture of isomers or a pharmaceutically acceptable salt, or solvate thereof together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease. In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral: using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the presents invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carder will form a gel in the nasal cavity. The powder composition may be presented in unit dose form for example in capsules or cartridges of e.g., gelatin or blister packs from which the powder may be administered by means of an inhaler.

The compounds of the present invention can be formulated in transdermal or subcutaneous drug delivery devices. These delivery systems are advantageous when sustained release of the compound is necessary and when patient compliance with a treatment regimen is crucial. Compounds in a transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington, (1995) *The Science and Practice of Pharmacy* (1995), edited by E. W. Martin, Mack Publishing Company, 19th edition, Easton, Pa. Representative pharmaceutical formulations containing a compound of the present invention are described in Examples 9–15.

EXAMPLES

The following preparations and examples are given to enable those skilled in the art to more clearly understand and to practice the present invention. They should not be considered as limiting the scope of the invention, but merely as being illustrative and representative thereof.

PREPARATION 1

Preparation of a Compound of Formula 1

4-(5-oxo-[1,4]oxazepan-4-yl)-butyraldehyde

To a stirred suspension of sodium hydride (0.9 g, 37.5 mmole) in dimethylformamide (50 mL) was added 1,4-oxazepan-2-one (30 mmole). The mixture was stirred at room temperature for 15 minutes, and then 5-bromo-1-pentene (5.03 g, 33.7 mmole) was added slowly. The reaction mixture was stirred at room temperature for 30 minutes, and then at 80° C. for 16 hours. The solvent was removed under reduced pressure and water was added to the residue. The mixture was extracted with diethyl ether, the organic phase was washed with water, dried (magnesium sulfate) and concentrated to give 1-pent-4-enyl-oxazepan-2-one (5.5 g,) as an oil.

Osmium tetroxide (17 mg, 0.07 mmole) was added to 1-pent-4-enyl-oxazepan-2-one (5.5 g, 28.3 mmole) in a mixture of tetrahydrofuran (100 mL) and water (50 mL) under ambient water bath cooling. The mixture was stirred for 5 minutes and solid sodium periodate (15.11 g, 70.65 mmole) was added in portions over 15 minutes. The reaction mixture was stirred for 3 hours and filtered. The filtrate was concentrated, saturated with solid sodium chloride, and extracted with methylene chloride. The organic phase was dried (magnesium sulfate) and concentrated. Purification by silica gel chromatography, eluting with chloroform, gave 4-(2-oxo-oxazepan-1-yl)-butyraldehyde (4.6 g).

Similarly, following the, procedure described above in Preparation 1, but optionally replacing 1,4-oxazepan-2-one with other appropriate compounds of formula a and optionally replacing 5-bromo-1-pentene with other appropriate alkylating agents of the formula $L(CH_2)_nCH=CH_2$ wherein L is a leaving group such as halogen, and utilizing modifications known to those skilled in the art, the additional compounds of formula 1 were prepared:

5-oxo-4-(4-oxobutyl)-[1,4]diazepane-1-carboxylic acid tert-butyl ester.

PREPARATION 2

Alternative Preparation of a Compound of Formula 1

5-Oxo-4-(4-oxobutyl-[1,4]diazepane-1-carboxylic Acid Tert-butyl Ester

To a suspension of 60% sodium hydride in mineral oil (0.2 g, 5 mmole) in N,N-dimethylformamide (6 mL) was added 5-oxo-[1,4]diazepane-1-carboxylic acid tert-butyl ester (1.0 g, 4.67 mmole). The reaction mixture was warmed at 50° C. for 5 minutes, and then at room temperature for 15 minutes. To the resulting solution was added 4-bromobutyraldehyde dimethyl acetal (0.99 g, 5 mmole). After the reaction mixture was stirred at room temperature for 16 hours, the solvent was removed, and the residue was partitioned between water and ethyl acetate. The organic phase was washed with water, dried (magnesium sulfate), and concentrated. The residue was dissolved in diethyl ether, and the suspension was filtered, and the filtrate was concentrated. Purification by silica gel chromatography, eluting with 2% methanol in chloroform, gave 4-(4,4-dimethoxybutyl)-5-oxo-[1,4]diazepane-1-carboxylic acid tert-butyl ester (0.8 g,) as a heavy syrup. Nmr: (chloroform-a) δ (ppm) 1.49, s, (9H); 2.64, m, 3H; 3.32, s (3H); 4.37, m, (1H).

A solution of 4-(4,4-dimethoxybutyl)-5-oxo-[1,4] diazepane-1-carboxylic acid tert-butyl ester (3 g, 9.08 mmole) in glacial acetic acid containing 0.5 mL water (10 mL) was stirred at room temperature for 24 hours. The solution was concentrated at 35° C. under reduced pressure, and the residue was partitioned between saturated aqueous sodium bicarbonate and diethyl ether. The organic phase was dried (magnesium sulfate), concentrated, and the residue recrystallized from diethyl ether/hexane to give 5-oxo-4-(4-oxobutyl)-[1,4]diazepane-1-carboxylic acid tert-butyl ester (0.85 g,), m.p. 86–87° C.

PREPARATION 3

Alternative Preparation of Compounds of Formula 1

To an ice-cooled solution of 1.93M phosgene in toluene (31 mL, 60 mmole) was added dropwise a solution of 5-chloro-1-pentanol (4.9 g, 40 mmole) and N,N-diethylaniline (5.97 g, 40 mmole) in toluene (40 mL). The reaction mixture was stirred at ambient temperature for 4 hours. The mixture was filtered, and the filtrate was concentrated. The residue was taken up in ethyl acetate, filtered, and the solution was added dropwise to an ice-cooled solution of 4-aminobutyraldehyde diethylacetal (7.09 g, 44 mmole) and triethylamine (4.45 g, 44 mmole) in ethyl acetate (60 mL). The reaction mixture was stirred at room temperature for 15 hours, filtered and concentrated. Purification by silica gel chromatography, eluting with 10% ethyl acetate in hexane, gave (4,4-diethoxybutyl)carbamic acid 5-chloro-pentyl ester (11.4 g,) as an oil.

To a solution of (4,4-diethoxybutyl)carbamic acid 5-chloro-pentyl ester (11.4 g, 44 mmole) dissolved in N,N-dimethylformamide (100 mL) was added de-oiled sodium hydride (1.01 g, 42.3 mmole). The reaction mixture was stirred for 15 hours at room temperature, and then at 70 °C. for 3 hours. The mixture was diluted with water, saturated aqueous sodium chloride was added, and extracted with diethyl ether. The organic phase was washed with water, dried (magnesium sulfate), and concentrated. Purification by silica gel chromatography, gave 3-(4,4-diethoxybutyl)-[1,3] oxazocan-2-one (2.03 g) as a viscous oil.

A mixture of 3-(4,4-diethoxybutyl)-[1,3]oxazocan-2-one (2 g, 7.3 mmole) and 1.5 g Dowex 50W2-200 ion exchange resin in 3% aqueous tetrahydrofuran (30 mL) was heated under reflux for 24 hours. The mixture was filtered, and the filtrate was concentrated and dissolved in dichloromethane. The solution was dried with magnesium sulfate and concentrated to give 4-(2-oxo-[1,3]oxazocan-3-yl)-butyraldehyde (1.45 g) as a viscous oil which solidified.

3-(2-oxo-Tetrahydropyrimidin-1-yl)-propionaldehyde

To a stirred and ice-cooled solution of 3-aminopropionaldehyde diethylacetal (5.88 g, 40 mmole) in diethyl ether (35 mL) was added dropwise 3-chloropropyl isocyanate (4.78 g, 40 mmole). The reaction mixture was stirred at room temperature for 4 hours. The mixture was concentrated and dissolved in N,N-dimethylformamide (40 mL). To this solution was added de-oiled sodium hydride (0.96 g, 40 mmole). The reaction mixture was stirred at 70° C. for 18 hours, concentrated, taken up in diethyl ether (40 mL), and filtered. The filtrate was concentrated and purified by silica gel chromatography, eluting with hexane-ethyl acetate-methanol (10:9.7:0.3), gave 1-(3,3-diethoxypropyl)-tetrahydropyrimidin-2-one (9.05 g) as an oil.

A mixture of 1-(3,3-diethoxypropyl)-tetrahydropyrimidin-2-one (1 g, 4.35 mmole), and 1.0 g Dowex 50W2-200 ion exchange resin in 3% aqueous tetrahydrofuran (30 mL) was heated under reflux for 24 hours. The mixture was filtered, the filtrate was concentrated and the residue dissolved in dichloromethane (30 mL), dried with magnesium sulfate, and concentrated to give 3-(2-oxo-tetrahydropyrimidin-1-yl)-propionaldehyde (0.46 g).

PREPARATION 4

Preparation of a Compound of Formula 2 ($R^1$, $R^2$= H, $R^3$=propyl, p=2)

Propyl-(1,2,3,4-Tetrahydro-naphthalen-2-yl)-amine

To a solution of 3,4-dihydro-1-H-naphthalen-2-one (5 g, 34 mmol) in 1,2-dichloroethane (250 mL), propyl amine (2.8 mL, 34 mmol) was added, followed by addition of sodium triacetoxyborohydride (22 g, 102 mmol). The reaction was stirred at ambient temperature under nitrogen for 24 hours, at which time it was concentrated in vacuo. The remaining solid was partitioned between 1 M sodium hydroxide and ethyl acetate. The ethyl acetate was washed with brine, dried over magnesium sulfate, and filtered. The filtrate was acidified with 1 M HCl in ether and 6.3 g of propyl-(1,2,3,4-tetrahydro-naphthalen-2-yl)-amine was collected as a pale pink precipitate.

Example 1

Preparation of a Compound of Formula IB as Described in Scheme B

3-{4-[(7-Methoxy-1,2,3,4-tetrahydro-naphthalen-2-yl)-propyl-amino]-butyl}-[1,31]oxazinan-2-one (19)

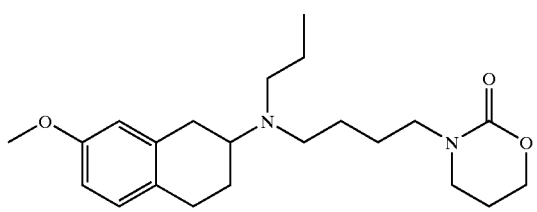

To a solution of 7-Methoxy-3,4-dihydro-1-H-naphthalen-2-one (5.0 g, 28.4 mmol) and propylamine (2.8 mL, 34 mmol, 1.2 eq) in 1,2-dichloroethane (1 50 mL) under inert atmosphere was added sodium triacetoxyborohydride (15 g, 71 mmol, 2.5 eq) in a single portion. The reaction was allowed to stir at room temperature for 20h then concentrated in-vacuo. The residue was partitioned between 10% aq. KOH (150 mL) and ethyl acetate (75 mL). The organic layer was washed with brine, dried and concentrated. The resulting material was dissolved in diethyl ether (100 mL) and treated with 1M HCl in ether (28.4 ML). The solid was collected and dried under vacuum to afford 6.23 g of (7-methoxy-1,2,3,4-tetrahydro-naphthalen-2-yl-propyl-amine as hydrochloride salt.

To (7-methoxy-1,2,3,4-tetrahydro-naphthalen-2-yl)-propyl-amine (ca.13 mg 50 umole), was added 440 µL solution of 4-(2-oxo-[1,3]oxazinan-3-yl)-butyraldehyde (0.125 M in 1,2 dichloroethane), 30 µL diisopropylethylamine (DIEA) and 300 µL of 0.25 M slurry of sodium triacetoxyborohydride in 1,2 dichloroethane. The reaction was shaken at room temperature for 48 h. After quenching with 2 mL 2% NaOH, the reaction mixture was transferred along with 0.5 mL water and ethyl acetate to workup flasks. The organic phase was washed, dried and concentrated. Purification by chromatography yielded 3-{4-[(7-methoxy-1,2,3,4-tetrahydro-naphthalen-2-yl)-propyl-amino]-butyl}-[1,3]oxazinan-2-one 19, MS: 375 ([M+H]$^+$).

Similarly, following the procedure described above in Example 1, but optionally replacing 4-(2-oxo-[1,3] oxazinan-3-yl)-butyraldehyde with other appropriate compounds of formula 1 b and optionally replacing 7-methoxy-1,2,3,4-tetrahydro-naphthalen-2-yl)-propyl-amine with other appropriate compounds of formula 2, and utilizing modifications known to those skilled in the ah, the additional compounds of Formula I wherein X is O, were prepared as trifluoroacetic acid salts:

3-{4-[(7-methoxy-1,2,3,4-tetrahydro-naphthalen-2-yl)-propyl-amino]-butyl}-[1,3]oxazepan-2-one 20, MS: 389 ([M+H]$^+$);

3-{4-[(6,7-dimethoxy-1,2,3,4-tetrahydro-naphthalen-2-yl)-propyl-amino]-butyl}-[1,3]oxazepan-2-one 28, MS: 419 ([M+H]$^+$);

3-{4-[(6,7-dimethoxy-1,2,3,4-tetrahydro-naphthalen-2-yl)-propyl-amino]-butyl}-[1,3]oxazinan-2-one 29, MS: 405 ([M+H]$^+$); 3-{4-[(6,7-dimethoxy-1,2,3,4-tetrahydro-naphthalen-2-yl)-propyl-amino]-butyl}-[1,3]oxazocan-2-one 31, MS: 403 ([M+H]$^+$);

3-{4-[(5,7-difluoro-1,2,3,4-tetrahydro-naphthalen-2-yl)-propyl-amino]-butyl}-[1,3]oxazinan-2-one 57, MS: 381 ([M+H]$^+$);

3-{4-[(5,7-difluoro-1,2,3 4-tetrahydro-naphthalen-2-yl)-propyl-amino]-butyl}-[1,3]oxazepan-2-one 58, MS: 395 ([M+H]$^+$);

3-{4-[(5,7-difluoro-1,2,3,4-tetrahydro-naphthalen-2-yl)-propyl-amino]-butyl}-[1,3]oxazocan-2-one 60, MS: 409 ([M+H]$^+$);

3-{4-[(7-nitro-1,2,3,4-tetrahydro-naphthalen-2-yl)-propyl-amino]-butyl}-[1,3]oxazepan-2-one 69, MS: 404 ([M+H]$^+$);

3-{4-[(7-nitro-1,2,3,4-tetrahydro-naphthalen-2-yl)-propyl-amino]-butyl}-[1,3]oxazinan-2-one 70, MS: 390 ([M+H]$^+$);

3-{4-[(7-ethoxy-1,2,3,4-tetrahydro-naphthalen-2-yl)-propyl-amino]-butyl}-[1,3]oxazinan-2-one 118, MS: 389 ([M+H]$^+$);

3-{4-[(6-ethoxy-1,2,3,4-tetrahydro-naphthalen-2-yl)-propyl-amino]-butyl}-[1,3]oxazepan-2-one 145, MS: 403 ([M+H]$^+$);

3-{4-[(6-ethoxy-1,2,3,4-tetrahydro-naphthalen-2-yl)-propyl-amino]-butyl}-[1,3]oxazinan-2-one 147, MS: 389 ([M+H]$^+$);

3-{4-[(6-bromo-1,2,3,4-tetrahydro-naphthalen-2-yl)-propyl-amino]-butyl}-[1,3]oxazinan-2-one 161, MS: 425 ([M+H]$^+$);

3-{4-[(6-bromo-1,2,3,4-tetrahydro-naphthalen-2-yl)-propyl-amino]-butyl}-[1,3]oxazepan-2-one 162, MS: 439 ([M+H]$^+$); or 3-{4-[(6,7-dimethoxy-1 2,3,4-tetrahydro-naphthalen-2-yl)-propyl-amino]-butyl}-[1,3]oxazepan-2-one 174, MS: 419 ([M+H]$^+$).

Example 2

Preparation of a Compound of Formula IC as Described in Scheme C

1-{4-[(7-Methoxy-1,2,3,4-tetrahydro-naphthalen-2-yl)-propyl-amino]-butyl}-[1,4]diazegan-2-one (3)

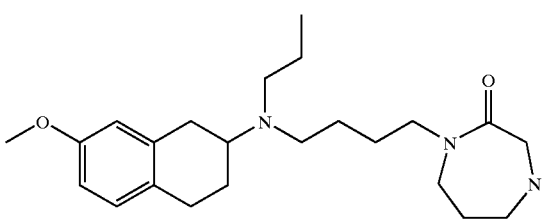

To a solution of (7-methoxy-1,2,3,4-tetrahydro-naphthalen-2-yl)-propyl-amine hydrochloride prepared as described in Example 1 (500 mg, 2 mmol, 1 eq) and triethylamine (0.3 mL, 2.2 mmol, 1.1 eq.) in 1,2-dichlororethane (20 mL) under inert atmosphere was added the 3-oxo-4-(4-oxo-butyl)-[1,4]diazepane-1-carboxylic acid tert-butyl ester (550 mg, 2 mmol, 1 eq.) in a single portion followed by the sodium triacetoxyborohydride (650 mg, 3 mmol, 1.5 eq.). The reaction was stirred at room temperature for 20 hr, concentrated in-vacuo and then partitioned between 10% KOH (40 mL) and ethyl acetate (75 mL), the organic layer was washed with brine, dried (MgSO$_4$) and concentrated. Purification by chromatography provided 858 mg of 4-{4-[(7-methoxy-1,2,3,4-tetrahydro-naphthalen-2-yl)-propyl-amino]-butyl}-3-oxo-[1,4]diazepane-1-carboxylic acid tert-butyl ester.

To a solution of 4-{4-[(7-methoxy-1,2,3,4-tetrahydro-naphthalen-2-yl)-propyl-amino]-butyl}-3-oxo-[1,4]diazepane-1-carboxylic acid tert-butyl ester (858 mg, 1.64 mmol) in methylene chloride (25 mL) was added trifluoroacetic acid (5 mL) in a single portion, and the reaction was stirred at room temperature for 30 min. The mixture was concentrated to dryness in-vacuo, dissolved in water and treated with 15% aq. KOH The solution was extracted with ethyl acetate, washed with brine, dried (MgSO$_4$) and concentrated to dryness. The free base (682 mg, 1.7 mmol) was taken up in diethyl ether (30 mL) and treated with 1M HCl/ether (3.4 mL). The solid was collected and dried under vacuum to afford the product 3 as a dihydrochloride (767 mg, 98% yield), MS 374 ([M+H]$^+$).

Similarly, following the procedures described above in Example 2, but optionally replacing 3-oxo-4-(4-oxobutyl)-[1,4]diazepane-1-carboxylic acid tert-butyl ester with other appropriate compounds of formula 1 d and optionally replacing (7-methoxy-1,2,3,4-tetrahydro-naphthalen-2-yl)-propyl-amine with other appropriate compounds of formula 2, and utilizing modifications known to those skilled in the art, the additional compounds of Formula I wherein Y is NH were prepared:

- 1-{4-[(6-methoxy-1,2,3,4-tetrahydro-naphthalen-2-yl)-propyl-amino]-butyl}-[1,4]diazepan-2-one 1, MS: 388 ([M+H]$^+$);
- 1-{4-[(7-methoxy-1,2,3,4-tetrahydro-naphthalen-2-yl)-propyl-amino]-butyl}-piperazin-2-one 12, MS: 374 ([M+H]$^+$);
- 1-{4-[ethyl-(7-methoxy-1,2,3,4-tetrahydro-naphthalen-2-yl)-amino]-butyl}-[1,4]diazepan-2-one 15, MS: 374 ([M+H]$^+$);
- 1-{3-[(7-methoxy-1,2,3,4-tetrahydro-naphthalen-2-yl)-propyl-amino]-propyl}-[1,4]diazepan-2-one 23, MS: 374 ([M+H]$^+$);
- 1-{4-[(7-methanesulfonyl-1,2,3,4-tetrahydro-naphthalen-2-yl)-propyl-amino]-butyl}-[1,4]diazepan-2-one 25, MS: 418 ([M+H]$^+$);
- 1-{4-[(7-isopropoxy-1,2,3,4-tetrahydro-naphthalen-2-yl)-propyl-amino]-butyl}-piperazin-2-one 36, MS: 402 ([M+H]$^+$);
- 1-{4-[(5,7-difluoro-1,2,3,4-tetrahydro-naphthalen-2-yl)-propyl-amino]-butyl}-piperazin-2-one 54, MS: 480 ([M+H]$^+$);
- 1-{4-[(5,7-difluoro-1,2,3,4-tetrahydro-naphthalen-2-yl)-propyl-amino]-butyl}-[1,4]diazepan-2-one 63, MS: 394 ([M+H]$^+$);
- 1-{4-[(7-nitro-1,2,3,4-tetrahydro-naphthalen-2-yl)-propyl-amino]-butyl}-[1,4]diazepan-2-one 72, MS: 403 ([M+H]$^+$);
- 1-{3-[(7-nitro-1,2,3,4-tetrahydro-naphthalen-2-yl)-propyl-amino]-propyl}-[1,4]diazepan-2-one 74, MS: 389 ([M+H]$^+$);
- 1-{4-[(7-Methoxy-1,2,3,4-tetrahydro-naphthalen-2-yl)-propyl-amino]-butyl}-piperazin-2-one 89, MS: 374 ([M+H]$^+$);
- 1-{4-[(7-methoxy-1,2,3,4-tetrahydro-naphthalen-2-yl)-propyl-amino]-butyl}-piperazin-2-one 91, MS: 374 ([M+H]$^+$);
- 1-{4-[(R)-(7-methoxy-1,2,3,4-tetrahydro-naphthalen-2-yl)-propyl-amino]-butyl}-[1,4]diazepan-2-one 92, MS: 388 ([M+H]$^+$);
- 1-{4-[(S)-(7-methoxy-1,2,3,4-tetrahydro-naphthalen-2-yl)-propyl-amino]-butyl}-[1,4]diazepan-2-one 93, MS: 388 ([M+H]$^+$);
- 1-{4-[(7-ethoxy-1,2,3,4–7tetrahydro-naphthalen-2-yl)-propyl-amino]-butyl)-piperazin-2-one 111, MS: 388 ([M+H]$^+$);
- 1-{4-[(7-ethoxy-1,2,3,4-tetrahydro-naphthalen-2-yl)-propyl-amino]-butyl}-[1,4]diazepan-2-one 112, MS: 402 ([M+H]$^+$);
- 1-{4-[(6-isopropoxy-1,2,3,4-tetrahydro-naphthalen-2-yl)-propyl-amino]-butyl}-piperazin-2-one 114, MS: 402 ([M+H]$^+$);
- 1-{4-[(6-ethoxy-1,2,3,4-tetrahydro-naphthalen-2-yl)-propyl-amino]-butyl}-piperazin-2-one 148, MS: 388 ([M+H]$^+$);
- 1-{5-[(6,7-dimethoxy-1,2,3,4-tetrahydro-naphthalen-2-yl)-propyl-amino]-pentyl}-piperazin-2-one 154, MS: 418([M+H]$^+$);
- 1-{5-[(6,7-dimethoxy-1,2,3,4-tetrahydro-naphthalen-2-yl)-propyl-amino]-pentyl}-[1,4]diazepan-2-one 155, MS: 432([M+H]$^+$);
- 1-(4-[(6,7-dimethoxy-1,2,3,4-tetrahydro-naphthalen-2-yl)-propyl-amino]-butyl}-[1,4]diazepan-2-one 156, MS: 418([M+H]$^+$);
- 1-{4-[(6,7-dimethoxy-1,2,3,4-tetrahydro-naphthalen-2-yl)-propyl-amino]-butyl}-piperazin-2-one 166, MS: 404([M+H]$^+$);
- 1-{4-[(7-bromo-1,2,3,4-tetrahydro-naphthalen-2-yl)-propyl-amino]-butyl}-[1,4]diazepan-2-one 171, MS: 436([M+H]$^+$); or
- 1-{4-[(6,7-dimethoxy-1,2,3,4-tetrahydro-naphthalen-2-yl)-propyl-amino]-butyl}-[1,4]diazepan-2-one 173, MS: 418([M+H]$^+$).

Example 3

Alternative Preparation of a Compound of Formula IC as Described in Scheme C 4-(2-Dimethylamino-ethanesulfonyl)-1-{4-[(7-methoxy-1,2,3,4-tetrahydro-naphthalen-2-yl)-propyl-amino]-butyl-}-[1,4]diazepan-2-one (64)

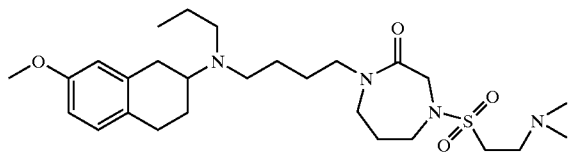

To (7-methoxy-1,2,3,4-tetrahydro-naphthalen-2-yl)-propyl-amine hydrochloride (150 mg, 0.3 mmol) and triethylamine (0.2 mL, 1.3 mmol) in methylene chloride (10 mL) under inert atmosphere was added 2-chloroethane sulfonyl chloride (0.03 mL, 0.3 mmol). The reaction mixture was allowed to stir at room temperature for 1 hour, and was quenched with 2% sodium carbonate. The organic layer was dried (MgSO$_4$), filtered and concentrated in-vacuo to afford 4-{4-[(7-methoxy-1,2,3,4-tetrahydro-naphthalen-2-yl)- propyl-amino]-butyl}-3-oxo-[1,4]diazepane-1-sulfonyl chloride as a yellow oil.

To 4-{4-[(7-methoxy-1,2,3,4-tetrahydro-naphthalen-2-yl)-propyl-amino]-butyl}-3-oxo-[1,4]diazepane-1-sulfonyl chloride (0.3 mmol) and triethylamine (0.1 mL, 0.6 mmol,) in methylene chloride (15 mL) under inert atmosphere was added dimethyl amine 2 M in THF (0.17 mL, 0.34 mmol). The reaction was allowed to stir at room temperature for 20 h, then concentrated in-vacuo. The remaining oil was purified over silica gel to afford a clear oil which was taken up in diethyl ether (10 mL) and treated with 1 M HCl in ether. The solid was collected and dried under vacuum to afford 4-(2-dimethylamino-ethanesulfonyl)-1-{4-[(7-methoxy-1,2,3,4-tetrahydro-naphthalen-2-yl)-propyl-amino]-butyl}-[1,4]diazepan-2-one as a dihydrochloride (83 mg) 64, MS: 523 ([M+H]$^+$).

Similarly, following the procedures described above in Example 3, but optionally replacing 1-{4-[(7-methoxy-1,2,3,4-tetrahydro-naphthalen-2-yl)-propyl-amino]-butyl}-[1,4]diazepan-2-one with other free amine compounds of Formula IC, and optionally replacing 2-chloroethane sulfonyl chloride with other appropriate acylating, alkylating, or sulfonylating agents, and utilizing modifications known to those skilled in the art, the additional compounds of Formula I wherein Y is NR$^4$ were prepared:

- 4-(2-dimethylamino-ethanesulfonyl)-1-{4-[(6-methoxy-1,2,3,4-tetrahydro-naphthalen-2-yl)-propyl-amino]-butyl}-[1,4]diazepan-2-one 2, MS: 523([M+H]$^+$);
- 4-(4-fluoro-benzoyl)-1-{4-[(7-methoxy-1,2,3,4-tetrahydro-naphthalen-2-yl)-propyl-amino]-butyl}-piperazin-2-one 121, MS: 496([M+H]$^+$);
- 4-(2,2-dimethyl-propionyl)-1-{4-[(7-methoxy-1,2,3,4-tetrahydro-naphthalen-2-yl)-propyl-amino]-butyl}-piperazin-2-one 122, MS: 458([M+H]$^+$);
- 4-isobutyryl-1-{4-[(7-methoxy-1,2,3,4-tetrahydro-naphthalen-2-yl)-propyl-amino]-butyl}-piperazin-2-one 123, MS: 444([M+H]$^+$);
- 1-{4-[(7-methoxy-1,2,3,4-tetrahydro-naphthalen-2-yl)-propyl-amino]-butyl}-4-(thiophene-2-carbonyl)-piperazin-2-one 124, MS: 484([M+H]$^+$);
- 4-{4-[(7-methoxy-1,2,3,4-tetrahydro-naphthalen-2-yl)-propyl-amino]-butyl}-3-oxo-piperazine-1-carboxylic acid diethylamide 125, MS: 473([M+H]$^+$);
- 4-{4-[(7-methoxy-1,2,3,4-tetrahydro-naphthalen-2-yl)-propyl-amino]-butyl}-3-oxo-piperazine-1-carboxylic acid dimethylamide 126, MS: 445([M+H]$^+$);
- 4-acetyl-1-{4-[(7-methoxy-1,2,3,4-tetrahydro-naphthalen-2-yl)-propyl-amino]-butyl}-piperazin-2-one 127, MS: 416([M+H]$^+$);
- 4-(3,5-dimethyl-isoxazole-4-carbonyl)-1-{4-[(7-methoxy-1,2,3,4-tetrahydro-naphthalen-2-yl)-propyl-amino]-butyl}-piperazin-2-one 128, MS: 497([M+H]$^+$);
- 1-{4-[(7-methoxy-1,2,3,4-tetrahydro-naphthalen-2-yl)-propyl-amino]-butyl}-4-(thiophene-2-sulfonyl)-piperazin-2-one 129, MS: 520([M+H]$^+$);
- 1-{4-[(7-methoxy-1,2,3,4-tetrahydro-naphthalen-2-yl)-propyl-amino]-butyl}-4-trifluoromethanesulfonyl-piperazin-2-one 130, MS: 506([M+H]$^+$);
- 4-benzenesulfonyl-1-{4-[(7-methoxy-1,2,3,4-tetrahydro-naphthalen-2-yl)-propyl-amino]-butyl}-piperazin-2-one 131, MS: 514([M+H]$^+$);
- 4-{4-[(7-methoxy-1,2,3,4-tetrahydro-naphthalen-2-yl)-propyl-amino]-butyl}-3-oxo-piperazine-1-sulfonic acid dimethylamide 132, MS: 481([M+H]$^+$);
- 4-{4-[(7-methoxy-1,2,3,4-tetrahydro-naphthalen-2-yl)-propyl-amino]-butyl}-3-oxo-piperazine-1-carboxylic acid phenylamide 133, MS: 493([M+H]$^+$);
- 4-{4-[(7-methoxy-1,2,3,4-tetrahydro-naphthalen-2-yl)-propyl-amino]-butyl}-3-oxo-piperazine-1-carboxylic acid ter-butylamide 134, MS: 473([M+H]$^+$);
- 4-{4-[(7-methoxy-1,2,3,4-tetrahydro-naphthalen-2-yl)-propyl-amino]-butyl}-3-oxo-piperazine-1-carboxylic acid methylamide 135, MS: 431 ([M+H]$^+$);
- 1-{4-[(7-methoxy-1,2,3,4-tetrahydro-naphthalen-2-yl)-propyl-amino]-butyl}-4-thiophen-2-ylmethyl-piperazin-2-one 136, MS: 470([M+H]$^+$);
- 4-ethyl-1-{4-[(7-methoxy-1,2,3,4-tetrahydro-naphthalen-2-yl)-propyl-amino]-butyl}-piperazin-2-one 137, MS: 470([M+H]$^+$);
- 4-(1-methanesulfonyl-piperidin-4-ylmethyl)-1-{4-[(7-methoxy-1,2,3,4-tetrahydro-naphthalen-2-yl)-propyl-amino ]-butyl}-piperazin-2-one 138, MS: 549([M+H]$^+$); or
- 4-methanesulfonyl-1-{4-[(7-methoxy-1,2,3,4-tetrahydro-naphthalen-2-yl)-propyl-amino]-butyl}-piperazin-2-one 139, MS: 452([M+H]$^+$).

Example 4

Alternative Preparation of a Compound of Formula IC as Described in Scheme C

4-{4-[(7-Methoxy-1,2,3,4-tetrahydro-naphthalen-2-yl)-propyl-amino]-butyl}-[1,4]oxazepan-3-one (17)

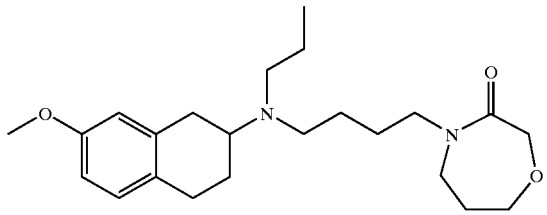

To (7-methoxy-1,2,3,4-tetrahydro-naphthalen-2-yl)-propyl-amine (ca.13 mg 50 μmole) as described in Example 1, was added 440 μL solution of 4-(2-oxo-[1,4]oxazepan-4-yl)-butyraldehyde (0.125 M in 1,2 dichloroethane), 30 μL diisopropylethylamine (DIEA) and 300 μL of 0.25 M slurry of sodium triacetoxyborohydride in 1,2 dichloroethane. The reaction was shaken at room temperature for 48 h. After quenching with 2 mL 2% NaOH, the reaction mixture was transferred along with 0.5 mL water and ethyl acetate to workup flasks. The organic phase was washed, dried and concentrated. Purification by chromatography yielded 4-{4-[(7-Methoxy-1,2,3,4-tetrahydro-naphthalen-2-yl)-propyl-amino]-butyl}-[1,4]oxazepan-3-one 17, MS: 389([M+H]$^+$);

Similarly, following the procedure described above in Example 4, but optionally replacing 4-(2-oxo-[1,4]oxazepan-4-yl)-butyraldehyde with other appropriate compounds of formula 1c and optionally replacing (7-methoxy-1,2,3,4-tetrahydro-naphthalen-2-yl)-propyl-amine with other appropriate compounds of formula 2, and utilizing modifications known to those skilled in the art, the additional compounds of Formula I wherein Y is O:

- 4-{4-[(6,7-dimethoxy-1,2,3,4-tetrahydro-naphthalen-2-yl)-propyl-amino]-butyl}-[1,4]oxazepan-5-one 27, MS: 419([M+H]$^+$);

4-{4-[(5,7-difluoro-1,2,3,4-tetrahydro-naphthalen-2-yl)-propyl-amino]-butyl}-[1,4]oxazepan-3-one 55, MS: ;395([M+H]$^+$);

1-{4-[(7-methoxy-1,2,3,4-tetrahydro-naphthalen-2-yl)-propyl-amino]-butyl}-4-(morpholine-4-carbonyl)-piperazin-2-one 120, MS: 487([M+H]$^+$); or 4-{4-[(6-ethoxy-l1,2,3,4-tetrahydro-naphthalen-2-yl)-propyl-amino]-butyl}-[1,4]oxazepan-3-one 144, MS: 403([M+H]$^+$).

Example 5

Preparation of a Compound of Formula ID as Described in Scheme D

4-{4-[(7-Methoxy-1,2,3,4-tetrahydro-naphthalen-2-yl)-propyl-amino]-butyl}-[1,4]diazepan-5-one (5)

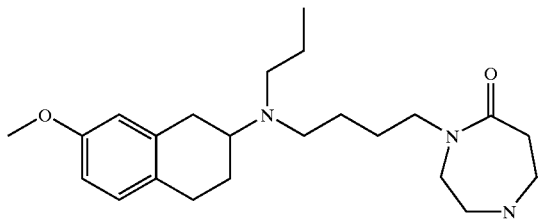

To a solution of (7-methoxy-1,2,3,4-tetrahydro-naphthalen-2-yl)-propyl-amine prepared as described in Example 1 (800 mg, 3.3 mmol, 1 eq) in 1,2-dichlororethane (40 mL) under inert atmosphere was added 5-oxo-4-(4-oxobutyl)-[1,4]diazepane-1-carboxylic acid tert-butyl ester (1.0 g, 3.6 mmol, 1.1 eq.) in a single portion followed by the sodium triacetoxyborohydride (1.7 g, 8.25 mmol, 2.5 eq.). The reaction was stirred at room temperature for 20 hr, concentrated in-vacuo and then partitioned between 10% KOH (50 mL) and ethyl acetate (100 mL). The organic layer was washed with brine, dried (MgSO$_4$) and concentrated. Purification by silica gel chromatography gave 1.1 g of 4-{4-[(7-methoxy-1,2,3,4-tetrahydro-naphthalen-2-yl)-propyl-amino]-butyl}-5 -oxo-[1,4]diazepane-1-carboxylic acid tert-butyl ester.

To 4-{4-[(7-methoxy-1,2,3,4-tetrahydro-naphthalen-2-yl)-propyl-amino]-butyl)-5-oxo-[1,4]diazepane-1-carboxylic acid tert-butyl ester (800 mg, 1.64 mmol) in methylene chloride (15 mL) was added trifluoroacetic acid (5 mL) in a single portion and the reaction was stirred at room temperature for 30 min. The mixture was concentrated to dryness in-vacuo, dissolved in water (40 mL) and treated with 15% aq. KOH (20 mL). The solution was extracted with ethyl acetate, washed with brine, dried (MgSO$_4$) and concentrated in-vacuo. The free base (636 mg, 1.64 mmol) was taken up in diethyl ether (30 mL) and treated with 1M HCl in ether (3.3 mL). The solid was collected and dried under vacuum to afford 732 mg of 4-{4-[(7-methoxy-1,2,3,4-tetrahydro-naphthalen-2-yl)-propyl-amino]-butyl}-[1,4]diazepan-5-one 5 as a dihydrochloride salt. MS: 374([M+H]$^+$).

Similarly, following the procedures described above in Example 5, but optionally replacing 5-oxo-4-(4-oxobutyl)-[1,4]diazepane-1-carboxylic acid tert-butyl ester with other appropriate compounds of formula 1f and optionally replacing (7-methoxy-1,2,3,4-tetrahydro-naphthalen-2-yl)-propyl-amine with other appropriate compounds of formula 2, and utilizing modifications known to those skilled in the art, the additional compounds of Formula I wherein Z is NH were prepared:

4-{4-[(6-methoxy-1,2,3,4-tetrahydro-naphthalen-2-yl)-propyl-amino]-butyl}-[1,4]diazepan-5-one 4, MS: 388 ([M+H]$^+$);

N(2-{ethyl-[4-(7-oxo-[1,4]diazepan-1-yl)-butyl]-amino}-indan-5-yl)-4-methanesulfonyl-benzamide 7, MS: 388 ([M+H]$^+$);

4-(4-{propyl-[6-(thiazole-2-sulfonyl)-1,2,3,4-tetrahydro-naphthalen-2-yl]-amino}-butyl)-[1,4]diazepan-5-one 8, MS: 505([M+H]$^+$);

4-{4-[ethyl-(5-methoxy-indan-2-yl)-amino]-butyl}-[1,4]diazepan-5-one 9, MS: 360([M+H]$^+$);

4-{4-[(6,7-dimethoxy-1,2,3,4-tetrahydro-naphthalen-2-yl)-propyl-amino]-butyl}-[1,4]diazepan-5-one 10, MS: 418([M+H]$^+$);

4-[4-(ethyl-indan-2-yl-amino)-butyl]-[1,4]diazepan-5-one 11; MS: 330([M+H]$^+$).

1-{4-[(7-methoxy-1,2,3,4-tetrahydro-naphthalen-2-yl)-propyl-amino]-butyl}-piperazin-2-one 13, MS: 374 ([M+H]$^+$);

4-(4-[ethyl-(7-methoxy-1,2,3,4-tetrahydro-naphthalen-2-yl)-amino]-butyl}-[1,4]diazepan-5-one 16, MS: 374 ([M+H]$^+$);

4-{4-[(7-isopropoxy-1,2,3,4-tetrahydro-naphthalen-2-yl)-propyl-amino]-butyl}-[1,4]diazepan-5-one 22, MS: 416([M+H]$^+$);

methanesulfonic acid 7-{[4-(7-oxo-[1,4]diazepan-1-yl)-butyl]-propyl-amino}-5,6,7,8-tetrahydro-naphthalen-2-yl ester 38, MS: 452([M+H]$^+$);

ethanesulfonic acid 7-{[4-(7-oxo-[1,4]diazepan-1-yl)-butyl]-propyl-amino}-5,6,7,8-tetrahydro-naphthalen-2-yl ester 39, MS: 466([M+H]$^+$);

propane-1-sulfonic acid 7-{[4-(7-oxo-[1,4]diazepan-1-yl)-butyl]-propyl-amino}-5,6,7,8-tetrahydro-naphthalen-2-yl ester 40, MS: 480([M+H]$^+$);

propane-2-sulfonic acid 7-{[4-(7-oxo-[1,4]diazepan-1-yl)-butyl]-propyl-amino}-5,6,7,8-tetrahydro-naphthalen-2-yl ester 41, MS: 480([M+H]$^+$);

trifluoro-methanesulfonic acid 7-{[4-(7-oxo-[1,4]diazepan-1-yl)-butyl]-propyl-amino}-5,6,7,8-tetrahydro-naphthalen-2-yl ester 42, MS: 506([M+H]$^+$);

benzenesulfonic acid 7-{[4-(7-oxo-[1,4]diazepan-1-yl)-butyl]-propyl-amino}-5,6,7,8-tetrahydro-naphthalen-2-yl ester 43, MS: 514([M+H]$^+$);

thiophene-2-sulfonic acid 7-{[4-(7-oxo-[1,4]diazepan-1-yl)-butyl]-propyl-amino}-5,6,7,8-tetrahydro-naphthalen-2-yl ester 44, MS: 520([M+H]$^+$);

phenyl-methanesulfonic acid 7-{[4-(7-oxo-[1,4]diazepan-1-yl)-butyl]-propyl-amino}-5,6,7,8-tetrahydro-naphthalen-2-yl ester 45, MS: 528([M+H]$^+$);

3,5-dimethyl-isoxazole-4-sulfonic acid 7-{[4-(7-oxo-[1,4]diazepan-1-yl)-butyl]-propyl-amino}-5,6,7,8-tetrahydro-naphthalen-2-yl ester 46, MS: 533([M+H]$^+$);

4-methoxy-benzenesulfonic acid 7-{[4-(7-oxo-[1,4]diazepan-1-yl)-butyl]-propyl-amino}-5,6,7,8-tetrahydro-naphthalen-2-yl ester 47, MS: 544([M+H]$^+$);

4-chloro-benzenesulfonic acid 7-{[4-(7-oxo-[1,4]diazepan-1-yl)-butyl]-propyl-amino}-5,6,7,8-tetrahydro-naphthalen-2-yl ester 48, MS: 548([M+H]$^+$);

4-chloro-benzenesulfonic acid 7-{[4-(7-oxo-[1,4]diazepan-1-yl)-butyl]-propyl-amino}-5,6,7,8-tetrahydro-naphthalen-2-yl ester 49 MS: 548([M+H]$^+$);

3-chloro-benzenesulfonic acid 7-{[4-(7-oxo-[1,4]diazepan-1-yl)-butyl]-propyl-amino}-5,6,7,8-tetrahydro-naphthalen-2-yl ester 50, MS: 548([M+H]$^+$);

dimethyl-sulfamic acid 7-{[4-(7-oxo-[1,4]diazepan-1-yl)-butyl]-propyl-amino}-5,6,7,8-tetrahydro-naphthalen-2-yl ester 51, MS: 481 ([M+H]⁺);

pyrrolidine-1-sulfonic acid 7-{[4-(7-oxo-[1,4]diazepan-1-yl)-butyl]-propyl-amino}-5,6,7,8-tetrahydro-naphthalen-2-yl ester 52, MS: 507([M+H]⁺);

4-{4-[(5,7-Difluoro-1,2,3,4-tetrahydro-naphthalen-2-yl)-propyl-amino]-butyl}-[1,4]diazepan-5-one 61, MS: 494([M+H]⁺);

4-{4-[(7-Hydroxy-1,2,3,4-tetrahydro-naphthalen-2-yl)-propyl-amino]-butyl}-[1,4]diazepan-5-one 65, MS: 374([M+H]⁺);

1-Methyl-1H-imidazole-4-sulfonic acid 7-{[4-(7-oxo-[1,4]diazepan-1-yl)-butyl]-propyl-amino}-5,6,7,8-tetrahydro-naphthalen-2-yl ester 66, MS: 518([M+H]⁺);

4-{4-[(7-Phenoxy-1,2,3,4-tetrahydro-naphthalen-2-yl)-propyl-amino]-butyl}-[1,4]diazepan-5-one 67, MS: 450([M+H]⁺);

trifluoro-acetic acid; 4-{4-[(7-nitro-1,2,3,4-tetrahydro-naphthalen-2-yl)-propyl-amino]-butyl}-[1,4]diazepan-5-one 71, MS: 403([M+H]⁺);

4-{5-[(7-nitro-1,2,3,4-tetrahydro-naphthalen-2-yl)-propyl-amino]-pentyl}-[1,4]diazepan-5-one 73, MS: 417([M+H]⁺);

4-{4-[(7-ethoxy-1,2,3,4-tetrahydro-naphthalen-2-yl)-propyl-amino]-butyl}-[1,4]diazepan-5-one 75, MS: 402([M+H]⁺);

N-(7-{[4-(7-Oxo-[1,4]diazepan-1-yl)-butyl]-propyl-amino}-5,6,7,8-tetrahydro-naphthalen-2-yl)-propionamide 6, MS: 429([M+H]⁺);

cyclopropanecarboxylic acid (7-{[4-(7-oxo-[1,4]diazepan-1-yl)-butyl]-propyl-amino}-5,6,7,8-tetrahydro-naphthalen-2-yl)-amide 77, MS: 441 ([M+H]⁺);

N-(7-{[4-(7-oxo-[1,4]diazepan-1-yl)-butyl]-propyl-amino}-5,6,7,8-tetrahydro-naphthalen-2-yl)-isobutyramide 78 MS: 443([M+H]⁺);

2,2-dimethyl-N-(7-{[4-(7-oxo-[1,4]diazepan-1-yl)-butyl]-propyl-amino}-5,6,7,8-tetrahydro-naphthalen-2-yl)-propionamide 79, MS: 457([M+H]⁺);

3,3-dimethyl-N-(7-{[4-(7-oxo-[1,4]diazepan-1-yl)-butyl]-propyl-amino}-5,6,7,8-tetrahydro-naphthalen-2-yl)-butyramide 80, MS: 457([M+H]⁺);

pyrrolidine-1-sulfonic acid (7-{[4-(7-oxo-[1,4]diazepan-1-yl)-butyl]-propyl-amino}-5,6,7,8-tetrahydro-naphthalen-2-yl)-amide 81, MS: 506 ([M+H]⁺);

4-(4-{[7-(2,2-dimethyl-propylamino)-1,2,3,4-tetrahydro-naphthalen-2-yl]-propyl-amino}-butyl)-[1,4]diazepan-5-one 82, MS: 443 ([M+H]⁺);

4-{4-[(7-cyclohexylamino-1,2,3,4-tetrahydro-naphthalen-2-yl)-propyl-amino]-butyl}-[1,4]diazepan-5-one 83, MS: 455 ([M+H]⁺);

1-isopropyl-3-(7-{[4-(7-oxo-[1,4]diazepan-1-yl)-butyl]-propyl-amino}-5,6,7,8-tetrahydro-naphthalen-2-yl)-urea 84, MS: 458 ([M+H]⁺);

1-ter-butyl-3-(7-{[4-(7-oxo-[1,4]diazepan-1-yl)-butyl]-propyl-amino}-5,6,7,8-tetrahydro-naphthalen-2-yl)-urea 85, MS: 472 ([M+H]⁺);

1-benzoyl-3-(7-{[4-(7-oxo-[1,4]diazepan-1-yl)-butyl]-propyl-amino}-5,6,7,8-tetrahydro-naphthalen-2-yl)-urea 86, MS: 520 ([M+H]⁺);

4-{4-[(S)-(7-methoxy-1,2,3,4-tetrahydro-naphthalen-2-yl)-propyl-amino]-butyl}-[1,4]diazepan-5-one 87, MS: 388 ([M+H]⁺);

4-{5-[(R)-(7-methoxy-1,2,3,4-tetrahydro-naphthalen-2-yl)-propyl-amino]-pentyl}-[1,4]diazepan-5-one 88, MS: 402 ([M+H]⁺);

4-{4-[(7-methoxy-1,2,3,4-tetrahydro-naphthalen-2-yl)-propyl-amino]-butyl}-[1,4]diazepan-5-one 90, MS: 388 ([M+H]⁺);

ethanesulfonic acid 6-{[4-(7-oxo-[1,4]diazepan-1-yl)-butyl]-propyl-amino}-5,6,7,8-tetrahydro-naphthalen-2-yl ester 94, MS: 466 ([M+H]⁺);

propane-2-sulfonic acid 6-{[4-(7-oxo-[1,4]diazepan-1-yl)-butyl]-propyl-amino}-5,6,7,8-tetrahydro-naphthalen-2-yl ester 95, MS: 466 ([M+H]⁺);

benzenesulfonic acid 6-{[4-(7-oxo-[1,4]diazepan-1-yl)-butyl]-propyl-amino}-5,6,7,8-tetrahydro-naphthalen-2-yl ester 96, MS: 514 ([M+H]⁺);

phenyl-methanesulfonic acid 6-{[4-(7-oxo-[1,4]diazepan-1-yl)-butyl]-propyl-amino}-5,6,7,8-tetrahydro-naphthalen-2-yl ester 97, MS: 528 ([M+H]⁺);

4-methoxy-benzenesulfonic acid 6-{[4-(7-oxo-[1,4]diazepan-1-yl)-butyl]-propyl-amino}-5,6,7,8-tetrahydro-naphthalen-2-yl ester 98, MS: 544 ([M+H]⁺);

2-chloro-benzenesulfonic acid 6-{[4-(7-oxo-[1,4]diazepan-1-yl)-butyl]-propyl-amino}-5,6,7,8-tetrahydro-naphthalen-2-yl ester 99, MS: 548 ([M+H]⁺);

pyrrolidine-1-sulfonic acid 6-{[4-(7-oxo-[1,4]diazepan-1-yl)-butyl]-propyl-amino}-5,6,7,8-tetrahydro-naphthalen-2-yl ester 100, MS: 507 ([M+H]⁺);

methanesulfonic acid 6-{[4-(7-oxo-[1,4]diazepan-1-yl)-butyl]-propyl-amino}-5,6,7,8-tetrahydro-naphthalen-2-yl ester 101, MS: 452 ([M+H]⁺);

propane-1-sulfonic acid 6-{[4-(7-oxo-[1,4]diazepan-1-yl)-butyl]-propyl-amino}-5,6,7,8-tetrahydro-naphthalen-2-yl ester 102, MS: 480 ([M+H]⁺);

trifluoro-methanesulfonic acid 6-{[4-(7-oxo-[1,4]diazepan-1-yl)-butyl]-propyl-amino}-5,6,7,8-tetrahydro-naphthalen-2-yl ester 103, MS: 506 ([M+H]⁺);

1-methyl-1H-imidazole-4-sulfonic acid 6-{[4-(7-oxo-[1,4]diazepan-1-yl)-butyl]-propyl-amino}-5,6,7,8-tetrahydro-naphthalen-2-yl ester 104, MS: 518 ([M+H]⁺);

thiophene-2-sulfonic acid 6-{[4-(7-oxo-[1,4]diazepan-1-yl)-butyl]-propyl-amino}-5,6,7,8-tetrahydro-naphthalen-2-yl ester 105, MS: 520 ([M+H]⁺);

3,5-dimethyl-isoxazole-4-sulfonic acid 6-{[4-(7-oxo-[1,4]diazepan-1-yl)-butyl]-propyl-amino}-5,6,7,8-tetrahydro-naphthalen-2-yl ester 106, MS: 533 ([M+H]⁺);

4-chloro-benzenesulfonic acid 6-{[4-(7-oxo-[1,4]diazepan-1-yl)-butyl]-propyl-amino}-5,6,7,8-tetrahydro-naphthalen-2-yl ester 107, MS: 548 ([M+H]⁺);

3-chloro-benzenesulfonic acid 6-{[4-(7-oxo-[1,4]diazepan-1-yl)-butyl]-propyl-amino}-5,6,7,8-tetrahydro-naphthalen-2-yl ester 108, MS: 548 ([M+H]⁺);

dimethyl-sulfamic acid 6-{[4-(7-oxo-[1,4]diazepan-1-yl)-butyl]-propyl-amino}-5,6,7,8-tetrahydro-naphthalen-2-yl ester 109, MS: 548 ([M+H]⁺);

4-{4-[(7-ethoxy-1,2,3,4-tetrahydro-naphthalen-2-yl)-propyl-amino]-butyl}-[1,4]diazepan-5-one 110, MS: 402 ([M+H]⁺);

4-{4-[(6-isopropoxy-1,2,3,4-tetrahydro-naphthalen-2-yl)-propyl-amino]-butyl}-[1,4]diazepan-5-one 113, MS: 416 ([M+H]⁺); trifluoro-methanesulfonic acid 6-{[4-(7-oxo-[1,4]diazepan-1-yl)-butyl]-propyl-amino}-5,6,7,8-tetrahydro-naphthalen-2-yl ester 140, MS: 508 ([M+H]⁺);

4-{4-[(6-bromo-1,2,3,4-tetrahydro-naphthalen-2-yl)-propyl-amino]-butyl}-[1,4]diazepan-5-one 141, MS: 436 ([M+H]+);

4-{5-[(7-methoxy-1,2,3,4-tetrahydro-naphthalen-2-yl)-propyl-amino]-pentyl}-[1,4]diazepan-5-one 142, MS: 402 ([M+H]+);

4-{4-[(6-ethoxy-1,2,3,4-tetrahydro-naphthalen-2-yl)-propyl-amino]-butyl}-[1,4]diazepan-5-one 150, MS: 402 ([M+H]+);

4-{5-[(6-ethoxy-1,2,3,4-tetrahydro-naphthalen-2-yl)-propyl-amino]-pentyl}-[1,4]diazepan-5-one 152, MS: 416 ([M+H]+);

4-{3-[(6-ethoxy-1,2,3,4-tetrahydro-naphthalen-2-yl)-propyl-amino]-propyl}-[1,4]diazepan-5-one 153, MS: 388 ([M+H]+);

4-{5-[(7-methoxy-1,2,3,4-tetrahydro-naphthalen-2-yl)-propyl-amino]-pentyl}-[1,4]diazepan-5-one 157, MS: 436 ([M+H]+);

dimethyl-carbamic acid 7-{[4-(7-oxo-[1,4]diazepan-1-yl)-butyl]-propyl-amino}-5,6,7,8-tetrahydro-naphthalen-2-yl ester 167, MS: 445 ([M+H]+);

morpholine-4-carboxylic acid 7-{[4-(7-oxo-[1,4]diazepan-1-yl)-butyl]-propyl-amino}-5,6,7,8-tetrahydro-naphthalen-2-yl ester 168, MS: 487 ([M+H]+);

isopropyl-carbamic acid 7-{[4-(7-oxo-[1,4]diazepan-1-yl)-butyl]-propyl-amino}-5,6,7,8-tetrahydro-naphthalen-2-yl ester 169, MS: 459 ([M+H]+);

propyl-carbamic acid 7-{[4-(7-oxo-[1,4]diazepan-1-yl)-butyl]-propyl-amino}-5,6,7,8-tetrahydro-naphthalen-2-yl ester 170, MS: 459 ([M+H]+); or 4-{5-[(6,7-dimethoxy-1,2,3,4-tetrahydro-naphthalen-2-yl)-propyl-amino]-pentyl}-[1,4]diazepan-5-one 172, MS: 432 ([M+H]+).

Example 6

Alternative Preparation of a Compound of Formula ID as Described in Scheme D 1-(2-Dimethylamino-ethanesulfonyl)-4-{4-[(7-methoxy-1,2,3,4-tetrahydro-naphthalen-2-yl)-propyl-amino]-butyl}-[1,4]diazepan-5-one (24)

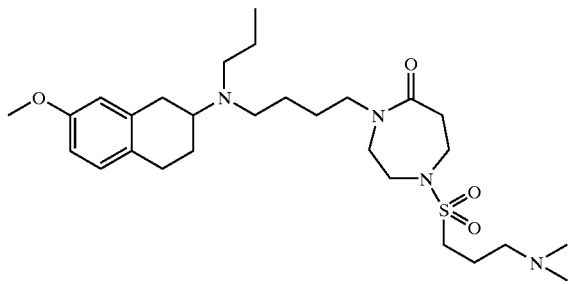

To a solution of 4-{4-[(7-methoxy-1,2,3,4-tetrahydro-naphthalen-2-yl)-propyl-amino]-butyl}-[1,4]diazepan-5-one dihydrochloride (732 mg, 1.6 mmol), prepared as in Example 1, and triethylamine (0.78 mL, 5.6 mmol) in methylene chloride (20 mL) under inert atmosphere was added 2-chloroethane sulfonyl chloride (0.17 mL, 1.6 mmol). The reaction mixture was allowed to stir at room temperature for 4 hours, and was quenched with 2% sodium carbonate. The organic layer was dried (MgSO4), filtered and concentrated in vacuo to afford the chloroethylsulfonamide as a yellow oil.

To the chloroethylsulfonamide (1.6 mmol) and triethylamine (0.5 mL, 3.6 mmol, 2.25 eq.) in methylene chloride (30 mL) under inert atmosphere was added dimethylamine hydrochloride (148 mg, 1.8 mmol). The reaction was allowed to stir at room temperature for 20 hours, then concentrated in vacuo. The remaining oil was chromatographed over silica gel to afford the free base as a clear oil. The free base (215 mg, 0.41 mmol) was taken up in diethyl ether and treated with 1M HCl in ether (0.82 mL). The solid was collected and dried under vacuum to afford 4-{4-[(7-methoxy-1,2,3,4-tetrahydro-naphthalen-2-yl)-propyl-amino]-butyl}-[1,4]diazepan-5-one 24 as a dihydrochloride (238 mg). (M+H)+=523.

Similarly, following the procedures described above in Example 6, but optionally replacing 4-{4-[(7-methoxy-1,2,3,4-tetrahydro-naphthalen-2-yl)-propyl-amino]-butyl}-[1,4]diazepan-5-one dihydrochloride with other free amine compounds of Formula ID, and optionally replacing chloroethylsulfonamide with other appropriate acylating, alkylating, or sulfonylating agents, and utilizing modifications known to those skilled in the art, the additional compounds of Formula I wherein Z is NR4 were prepared:

1-(2-dimethylamino-ethanesulfonylmethyl)-4-{4-[(6-methoxy-1,2,3,4-tetrahydro-naphthalen-2-yl)-propyl-amino]-butyl}-[1,4]diazepan-5-one 6, MS: 523 ([M+H]+).

Example 7

Alternative Preparation of a Compound of Formula ID as Described in Scheme D

4-{4-[(7-Methoxy-1,2,3,4-tetrahydro-naphthalen-2-yl)-propyl-amino]-butyl}-[1,4]oxazepan-5-one (18)

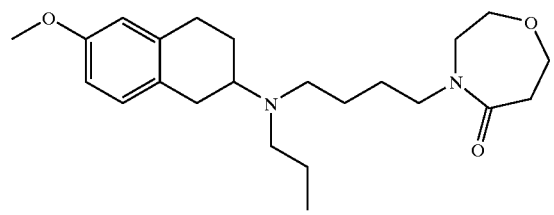

To (7-methoxy-1,2,3,4-tetrahydro-naphthalen-2-yl)-propyl-amine (ca. 13 mg 50 μmole) prepared as described in Example 1, was added 440 μL solution of 4-(6-oxo-[1,4]oxazepan-4-yl)-butyraldehyde (0.125 M in 11,2 dichloroethane), 30 μL diisopropylethylamine (DIEA) and 300 μL of 0.25 M slurry of sodium triacetoxyborohydride in 1,2 dichloroethane. The reaction was shaken at room temperature for 48 h. After quenching with 2 mL 2% NaOH, the reaction mixture was transferred along with 0.5 mL water and ethyl acetate to workup flasks. The organic phase was washed, dried and concentrated. Purification by chromatography yielded 3-{4-[(7-methoxy-1,2,3,4-tetrahydro-naphthalen-2-yl)-propyl-amino]-butyl}-[1,3]oxazinan-2-one 18, MS: 375 ([M+H]+).

Similarly, following the procedure described above in Example 7, but optionally replacing 4-(6-oxo-[1,4]oxazepan-4-yl)-butyraldehyde with other appropriate compounds of formula 1e and optionally replacing (7-methoxy-1,2,3,4-tetrahydro-naphthalen-2-yl)-propyl-amine with other appropriate compounds of formula 2, and utilizing modifications known to those skilled in the art, the additional compounds of Formula I wherein Z is O were prepared:

4-{4-[(6,7-dimethoxy-1,2,3,4-tetrahydro-naphthalen-2-yl)-propyl-amino]-buty})-[1,4]oxazepan-5-one 26 MS: 419 ([M+H]$^+$);4-{4-[(7-isopropoxy-1,2,3,4-tetrahydro-naphthalen-2-yl)-propyl-amino]-butyl}-[1,4]oxazepan-5-one 34, MS: 417 ([M+H]$^+$);

4-{4-[(5,7-difluoro-1,2,3,4-tetrahydro-naphthalen-2-yl)-propyl-amino]-butyl}-[1,4]oxazepan-5-one 56, MS: 395 ([M+H]$^+$);

4-{4-[(7-nitro-1,2,3,4-tetrahydro-naphthalen-2-yl)-propyl-amino]-butyl}-[1,4]oxazepan-5-one 68, MS: 404 ([M+H]$^+$);

4-{4-[(7-ethoxy-1,2,3,4-tetrahydro-naphthalen-2-yl)-propyl-amino]-butyl}-[1,4]oxazepan-5-one 116, MS: 403 ([M+H]$^+$);

4-{4-[(6-Ethoxy-1,2,3,4-tetrahydro-naphthalen-2-yl)-propyl-amino]-butyl}-[1,4]oxazepan-5-one 143, MS: 403 ([M+H]$^+$); or 4-{4-[(6-Bromo-1,2,3,4-tetrahydro-naphthalen-2-yl)-propyl-amino]-butyl}-[1,4]oxazepan-5-one 160, MS: 439 ([M+H]$^+$).

Example 8

Composition for Oral Administration

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 9

Composition for Oral Administration

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 10

Composition for Oral Administration

| Ingredient | Amount |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 mL |

Composition for Oral Administration

| Ingredient | Amount |
|---|---|
| Colorings | 0.5 mg |
| Distilled water | q.s. to 100 mL |

The ingredients are mixed to form a suspension for oral administration.

Example 11

Parenteral Formulation (IV)

| Ingredient | % wt/wt. |
|---|---|
| Active ingredient | 0.25 g |
| Sodium Chloride | qs to make isotonic |
| Water for injection to | 100 mL |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 12

Suppository Formulation

| Ingredient | % wt/wt. |
|---|---|
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 13

Topical Formulation

| Ingredients | grams |
|---|---|
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 14

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 15

Radioligand Binding Studies

The inhibitory activity of compounds of this invention in vitro was determined using a modification of the method described in Hegde, S. S. et al. (1997) *Br. J. Pharmacol.*, 120, 1409–1418.

Cell membranes from Chinese hamster ovary cells expressing the recombinant human muscarinic receptors ($m_1$–$m_5$) were employed. The assays were conducted with the radioligand [$^3$H]N-methyl scopolamine(0.4 nM, specific activity 84 Ci.mmol$^{+1}$) in a final volume of 0.25 mL Tris-Krebs buffer. Non-specific binding was defined with 1 $\mu$M atropine. Assays were performed using scintillation proximity assay technology. Competition-displacement curves were generated using 10 concentrations of test compounds and were analyzed by iterative curve fitting to a four parameter logistic equation. $pIC_{50}$ values (-log of the ICso) were converted to pKi values using the Cheng-Prusoff equation.

Compounds of this invention were active in this assay.

Example 16

Oxotremorine/Pilocarpine-Induced Salivation (OIS/PIS) Model in Anesthetized Rats Female Sprague-Dawley rats (Charles-River, 200–300 g) rats were anesthetized with urethane (1.5 g/kg, sc) and were tracheotomized. One femoral vein was cannulated for drug administration. After a one hour stabilization period, rats were pre-treated with methoctramine (only for 018) to antagonize $M_2$ receptor mediated bradycardia. Each animal was dosed, intravenously, with a single dose of the vehicle or the reference compound. Ten minutes later, pre-weighed cotton pads were placed in the animals mouth following which they were dosed with vehicle or oxotremorine (0.1 mg/kg, iv)/pilocarpine (1 mg/kg, iv). Fresh cotton pads were placed at 5 minutes post-oxotremorine/pilocarpine and saliva collected for an additional 5 minutes. The cotton pads (5 and 10-minute period) were then re-weighed to determine the amount of saliva secreted during the 10-minute period.

All oxotremorine/pilocarpine treated groups were compared using one-way analysis of variance. Pair-wise comparisons were made using Dunnett's test. The ranked data (non-parametric technique) or actual levels of the data (parametric technique) are applied in the analysis depending upon the results of the Bartlett's test, which tests homogeneity of variances. The vehicle/oxdtremorine group and vehicle/pilocarpine was compared to the vehicle/vehicle group using Wilcox on rank-sum test. An estimate of the $ID_{50}$ for each compound with respect to the 10 minute overall secretion weight for each animal was obtained. The sigmoidal model is in the form of $$Resp = min + (max - min)/(1 + (dose/ID_{50})^{**}N)$$

where $ID_{50}$ is the dose to achieve half the maximal response, N is the curvature parameter and max is the max response for the dose response curve. The minimum response was fixed at 0 in the model.

Compounds of this invention were active in this assay.

Example 17

Inhibition of Volume-Induced Contractions in Rats

The muscarinic receptor inhibitory activity of compounds of this invention in vivo was determined in rats using a modification of the method described in Hegde, S. S. et al. (1996) *Proceedings of the 26th Annual Meeting of the International Continence Society* (August 27th–30th), Abstract 126.

Female Sprague-Dawley rats were anesthetized with urethane and instrumented for intravenous administration of drugs and, in some cases, measurement of arterial pressure, heart rate and intra-bladder pressure. The effect of test compounds on volume-induced bladder contractions was determined in separate groups of animals. Volume-induced reflex bladder contractions were induced by filling the bladder with saline. The test compounds were administered intravenously in a cumulative manner at 10-minute intervals. Atropine (0.3 mg/kg, iv) was administered at the end of the study as a positive control.

Compounds of this invention were active in this assay.

Example 18

Anti-muscarinic Activity in Anesthetized Dogs

The muscarinic receptor inhibitory activity of compounds of this invention in vivo was determined in dogs using a modification of the method described in Newgreen, D. T. et al. (1996) *J. Urol.*, 155 (Suppl. 5), 1156.

Female beagles (Marshall Farms, North Rose, N.Y.) were fasted for 18 hours prior to the experiment; water was allowed ad libitum. On the day of the experiment, dogs were anesthetized and maintained on pentobarbital (36 mg/kg, iv initially, then 5–10 mg/kg, iv for maintenance). Intravenous fluids were also administered to the dog for the remainder of the experiment. The dogs were artificially ventilated, via an endotracheal tube, with an Harvard respirator (Model 613). Both femoral veins and one femoral artery was cannulated for drug ad ministration and blood pressure measurement, respectively. Blood pressure was measured with a Gould transducer (Model P23XL) and recorded on a Gould recorder (Model 3400). A sublingual incision was made to expose the left mandibular duct, which was then cannulated for the collection of saliva into pre-weighed vials. The left salivary gland was exposed via a submandibular incision. The chorda-lingual nerve was isolated and had a bipolar electrode placed on it for stimulation. Test responses to chorda-lingual nerve stimulation were obtained to confirm proper electrode placement.

After completion of surgery, physostigmine (180 $\mu$g/kg/hr, iv) (a cholinesterase inhibitor) was infused for the remainder of the experiment. Following a one hour stabilization period, two control chorda-lingual nerve stimulations were performed at 12 Hz, 10 V, 0.5 ms duration (Grass S48). The chorda-lingual nerve was stimulated for 20 seconds and 2 minutes, respectively, with a minimum of 1 0 minute interval between each set of stimulations. After two consistent control responses were obtained, the vehicle or the reference compound was dosed in a cumulative fashion, 3 minutes prior to each stimulation of the chorda-lingual nerve. Experiments in which consistent salivation responses could not be obtained were not included in the analysis.

Atropine (1.0 mg/kg, iv) was given as a positive control at the end of the study.

Mean arterial blood pressure was calculated as Diastolic arterial pressure+(Systolic arterial pressure−Diastolic arterial pressure)/3. Heart rate was derived from the pressure pulse. Saliva was collected in pre-weighed vials and weighed after each collection to determine the volume of saliva secreted. Inhibition of salivary gland responses were expressed as a percent of the effect of atropine (1 mg/kg, iv).

ED50 Estimation

For % max inhibition salivation, parameter estimation was performed using a nonlinear mixed model. The method was implemented using PROC NLIN initially and PROC MIXED iteratively. This procedure assumed the following sigmoidal dose-response model:

$$Response = Min + \frac{Max - Min}{1 + 10^{-\frac{(x-\mu)}{\sigma}}}$$

where response=% max inhibition bladder contraction at peak, x=$\log_{10}$ dose of treatment and the 4 parameters were: $\log_{10}$ ED50 ($\mu$), maximum and minimum response (Max and Min), and curvature: ($\sigma$). The minimum was assumed 0%. This method assumed compound symmetry for the covariance structure. It was an iterative curve-fitting procedure that accounted for the dependence between multiple measurements from the same animal, and estimated the desired parameters and their confidence limits by adjusting its error calculations to account for within subject correlation.

Baseline Comparisons

To compare each dose to baseline control for every variable, a two-way ANOVA with main effects of subject and treatment was performed, followed by a pair t-test at each dose level. If the overall treatment effect was not significant (p-value>0.05) in ANOVA, a Bonferroni adjustment for p-values was used for the p-value of pair t-test at each dose.

Compounds of this invention were active in this assay.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound comprising Formula I

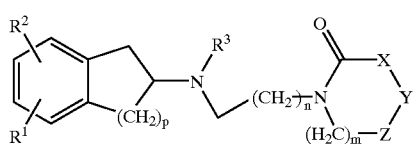

(I)

wherein:
$R^1$ and $R^2$ are independently in each occurrence hydrogen, halogen, $(C_{1-6})$-alkyl, —OR', —SR', —NR'R", —SOR', —SO$_2$R', —COOR', —OCOR', —OCONR'R", —OSO$_2$R', —OSO$_2$NR'R"; —NRSO$_2$R", —NR'COR", —SO$_2$NR'R", —SO$_2$(CH$_2$)$_{1-3}$CONR'R", —CONR'R", cyano, haloalkyl or nitro;

R' and R" are independently in each occurrence hydrogen, $(C_{1-6})$-alkyl, substituted lower alkyl, aryl, heterocyclyl, heteroaryl, aryl-$(C_{1-3})$-alkyl, heteroaryl-$(C_{1-3})$-alkyl, heterocyclyl-$(C_{1-3})$-alkyl, cycloalkylalkyl, cycloalkyl, or R' and R" together with the nitrogen to which they are attached form a 5- to 7-membered ring, optionally incorporating one additional ring heteroatom chosen from N, O or S(O)$_{0-2}$;

$R^3$ is selected from the group consisting of $(C_{1-6})$ alkyl, $(C_{1-6})$ alkenyl, $(C_{1-6})$ alkynyl, and cycloalkyl;

one of Y or Z is O and the other of Y or Z and X is CH$_2$;

wherein:
"substituted lower alkyl" means the lower alkyl having one to three substituents, selected from the group consisting of hydroxyl, alkoxy, amino, amido, carboxyl, acyl, halogen, cyano, nitro, thiol;

"heteroaryl" means the monovalent aromatic cyclic radical having one to three rings of four to eight atoms per ring, incorporating one or two heteroatoms (chosen from nitrogen, oxygen or sulfur), within the ring which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylainino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino;

"heterocyclyl" means the monovalent saturated cyclic radical, consisting of one or two rings, of three to eight atoms per ring, incorporating one or more ring heteroatoms (chosen from N, O or S(O)$_{0-2}$), and which can optionally be substituted with one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino;

"cycloalkyl" means the monovalent saturated carbocyclic radical consisting of one or two rings, of three to eight carbons per ring, which can optionally be substituted with one or two substitutents, selected from hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylamninocarbonyl, arylaminocarbonyl, alkylcarbonylamino, arylcarbonylamino;

p is an integer from 1 to 3 inclusive;
m is 2;
n is an integer from 1 to 6 inclusive; or,
individual isomers, racemic or non-racemic mixtures of isomers, or pharmaceutically acceptable salts or solvates, thereof.

2. The compound of claim 1, wherein p is 2.
3. The compound of claim 2, wherein n is 3.
4. The compound of claim 1 wherein Y is O and X and Z are CH$_2$.
5. The compound of claim 1 wherein Z is O and X and Y are CH$_2$.

6. The compound of claim 1, wherein m is 2, n is 3, and one of Y or Z is O and the other of Y or Z and X are CH$_2$.

7. The compound of claim 1 comprising 3-{4-[(6,7-dimethoxy-1,2,3,4-tetrahydro-naphthalen-2-yl)-propyl-amino]-butyl}-[1,3]oxazepan-2-one, or an individual isomer, a racemic or non-racemic mixture of isomers, or pharmaceutically acceptable salt or solvate thereof.

8. A pharmaceutical composition comprising a therapeutically effective amount of a compound of claim 1 in admixture with a pharmaceutically acceptable carrier.

9. The method of treatment of a disease state associated with smooth muscle disorders comprising diseases of the genitourinary or gastrointestinal tract, or a disease state comprising allergies, asthma, chronic obstructive pulmonary disease or pulmonary fibrosis comprising administering to a patient in need thereof a therapeutically effective amount of a compound of claim 1.

10. The method of treatment of claim 9, wherein said disease state associated with the genitourinary tract comprises overactive bladder, detrusor hyperactivity, urgency, frequency, reduced bladder capacity, incontinence episodes, changes in bladder capacity, micturition threshold, unstable bladder contractions, sphincteric spasticity, outlet obstruction, outlet insuffciency, pelvic hypersensitivity, idiopathic conditions or detrusor instability.

11. The method of treatment of claim 9, wherein the disease state comprises respiratory states from allergies, asthma, chronic obstructive pulmonary disease or pulmonary fibrosis.

12. The method of treatment of claim 9, wherein the disease state associated with gastrointestinal tract disorders comprises irritable bowel syndrome, diverticular disease, gastrointestinal hypermobility disorders or diarrhea.

13. A process for preparing a compound as claimed in claim 1 which process comprises reacting a compound having a general formula

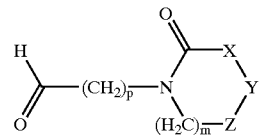

with a compound of general formula

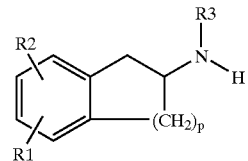

to provide a compound of Formula I

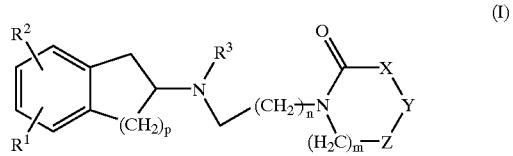

(I)

wherein R$^1$, R$^2$, R$^3$ p, m, n, X, Y, and Z are as defined in claim 1.

* * * * *

UNITED STATES PATENT AND TRADEMARK OFFICE
CERTIFICATE OF CORRECTION

PATENT NO. : 6,645,958 B2
DATED : November 11, 2003
INVENTOR(S) : Robert James Weikert, Anne Marie Madera and Russell Steven Stabler It is certified that error appears in the above-identified patent and that said Letters Patent is hereby corrected as shown below:

Column 45,
Line 65, "-NRSO2R"" should be changed to -- -NR'SO2R" --.

Column 46,
Line 24, "alkylainino" should be replaced with -- alkylamino --.
Line 63, "claim 2" should be replaced by -- claim 1 --.

Column 47,
Line 24, "insuffciency" should be replaced by -- insufficiency --.

Signed and Sealed this

Eighth Day of February, 2005

JON W. DUDAS
*Director of the United States Patent and Trademark Office*